United States Patent [19]

Brenner et al.

[11] Patent Number: 5,747,036
[45] Date of Patent: May 5, 1998

[54] METHODS AND COMPOSITIONS FOR DETECTING AND TREATING A SUBSET OF HUMAN PATIENTS HAVING AN AUTOIMMUNE DISEASE

[75] Inventors: Michael Brenner, Brookline; Harout Der Simonian, Wellesley, both of Mass.

[73] Assignees: Brigham & Women's Hospital; Dana Farber Cancer Institute, both of Boston, Mass.

[21] Appl. No.: 484,512

[22] Filed: Jun. 7, 1995

Related U.S. Application Data

[63] Continuation-in-part of Ser. No. 407,526, Mar. 16, 1995, abandoned, which is a continuation of Ser. No. 936,267, Aug. 26, 1992, Pat. No. 5,445,940, which is a continuation-in-part of Ser. No. 750,986, Aug. 28, 1991, abandoned.

[51] Int. Cl.$^6$ ............................................. A61K 39/395
[52] U.S. Cl. ............................ 424/144.1; 424/154.1; 424/173.1; 424/178.1
[58] Field of Search .................... 424/140.1, 144.1, 424/178.1, 154.1, 173.1

[56] References Cited

U.S. PATENT DOCUMENTS

| | | | |
|---|---|---|---|
| 4,550,086 | 10/1985 | Reinherz et al. | 436/506 |
| 4,657,760 | 4/1987 | Kung et al. | 424/85 |
| 4,713,332 | 12/1987 | Mak | 435/70 |
| 4,845,026 | 7/1989 | Kung et al. | 435/5 |
| 4,886,743 | 12/1989 | Hood et al. | 435/5 |
| 4,923,799 | 5/1990 | Mak | 435/6 |
| 5,024,940 | 6/1991 | Brenner et al. | 435/69.1 |
| 5,034,316 | 7/1991 | Weisbart et al. | 435/7.24 |

FOREIGN PATENT DOCUMENTS

| | | |
|---|---|---|
| 0 180 878 | 5/1986 | European Pat. Off. . |
| 0 340 109 | 11/1989 | European Pat. Off. . |
| WO 90/06758 | 6/1990 | WIPO . |
| WO 91/09623 | 7/1991 | WIPO . |
| 9304700 | 3/1993 | WIPO . |

OTHER PUBLICATIONS

Janson et al., *Blood*, 77, No. 8, 1776–1780 (Apr. 15, 1991).
Grunewald et al., *Scandinavian J. Immunol.*, 34:161–168 (1991).
Fraser et al., *Immunogenetics*, 28:108–116 (1988).
Brenner et al., *J. Immunol.* 138:1503–1508 (Mar. 1987).
Sim et al., *Nature*, 312:771–775 (Dec. 1984).
Brenner et al., *J. Exp. Med.*, 160:541–551 (Aug. 1984).
Janson et al., *Cancer Immunol. Immunother.*, 28:225–232 (1989).
Utsunomiya et al., *J. Immunol.* 143:2602–2608 (Oct. 15, 1981).
Jameson et al., *J. Immunol.*, 145:1324–1331 (Sep. 1, 1990).
Hannun et al., *Nature*, 312:65–67 (Nov. 1984).
Yoshikai et al., *J. Exp. Med.*, 164:90–103.
Kimura et al., *Eur. J. Immunol.*, 17:375–383 (1987).
Klein et al., *Proc. Natl. Acad. Sci., USA*, 84:6884–6888 (Oct. 1987).
Roman–Roman et al., *Eur. J. Immunol.*, 21:927–933 (1991).
Posnett et al., *J. Biol. Chem.*, 263(4):1719–1725 (1988).
Boylston et al., *J. Immunol.*, 137(2):741–744 (Jul. 15, 1986).
Kotzin et al., *J. Cellular Biochem.*, suppl. 15, p. 144 (Mar. 1991).
Cappellacci et al., *Clinical and Experimental Rheumatology*, 5:63 (1987).
Simons & Tait, *Detection of Immune–Associated Markers of Human Disease* (1984). Chapters 4–6.
D.C. Wraith, et al, Cell, 57, 709–715, 1989.

*Primary Examiner*—David Saunders
*Attorney, Agent, or Firm*—David G. Conlin; Ronald I. Eisenstein; David S. Resnick

[57] ABSTRACT

Provided are monoclonal antibodies, fragments, and derivatives thereof reactive with an epitope of the T cell receptor alpha chain variable region, Vα12.1, on human T lymphocytes. The monoclonal antibodies are reactive with approximately 2% of CD4$^+$ T lymphocytes and with approximately 5% of CD8$^+$ T lymphocytes in peripheral blood cells in normal individuals and define a subset of individuals afflicted with an autoimmune disease, especially rheumatoid arthritis, that exhibit increased expression of the Vα12.1 gene on CD8$^+$ peripheral blood T lymphocytes when compared to normal individuals. Methods for treating individuals afflicted with such an autoimmune disease using Vα12.1 specific reagents are described herein.

7 Claims, 11 Drawing Sheets

| | A | A | B | B | C | C | DR | DR | DQ | DQ |
|---|---|---|---|---|---|---|---|---|---|---|
| patient ML | X | 32 | 44 | 60 w3 | X | | 4 | 7 | 2 | 3 |
| B-LCL1 | 1 | 2 | 8 | 60 w3 | X | | 3 | 6 | 2 | 1 |
| B-LCL2 | 24 | 33 | 17 | 60 w3 | X | | 4 | 3 | 2 | X |
| B-LCL3 | 1 | 2 | 8 | 60 w3 | w7 | | 2 | 3 | 2 | 1 |

|     | ML  | LAU |
|-----|-----|-----|
| A   | X   | 2   |
| A   | 32  | 32  |
| B   | 44  | 51  |
| B   | 60  | 60  |
| C   | w3  | w3  |
| C   | X   | X   |
| DR  | 4   | 4   |
| DR  | 7   | 53  |
| DQ  | 2   | X   |
| DQ  | 3   | 3   |

METHODS AND COMPOSITIONS FOR DETECTING AND TREATING A SUBSET OF HUMAN PATIENTS HAVING AN AUTOIMMUNE DISEASE

CROSS REFERENCE TO RELATED APPLICATION

This application is a continuation-in-part of U.S. application Ser. No. 08/407,526, filed on Mar. 16, 1995 and now abandoned, which is a continuation of U.S. application Ser. No. 07/936,267, filed on Aug. 26, 1992 now U.S. Pat. No. 5,445,940, which is a continuation-in-part of U.S. application Ser. No. 07/750,986, filed on Aug. 28, 1991 and now abandoned.

GOVERNMENT RIGHTS IN INVENTION

This invention was made with the support of Government Grant AR39582 and Government Fellowship AR0806901 from the National Institutes of Health. The government of the United States of America has certain rights in this invention.

BACKGROUND OF THE INVENTION

1. Technical Field

This invention relates to the diagnosis and treatment of a subset of individuals afflicted with an autoimmune disease, especially rheumatoid arthritis, using a V$\alpha$12.1 T cell receptor specific-reagent. Expression of the V$\alpha$12.1 gene product on $CD8^+$ T lymphocytes is elevated in a subset of rheumatoid arthritis patients when compared to the expression of V$\alpha$12.1 on $CD8^+$ T lymphocytes of normal, healthy subjects that do not have the immune abnormality, thereby enabling the diagnosis and treatment of this subset of patients.

A higher level of assurance in the diagnosis of rheumatoid arthritis by V$\alpha$12.1 expansion can be made by determining that the expansion is clonal or oligoclonal and that the expansion correlates with the occurrence of the HLA-DQw2 allele in V$\alpha$12.1-elevated individuals.

2. Background Art

T cell precursors migrate from the bone marrow to the thymus where thymocytes begin to mature and express the T cell receptor for antigen. Through positive and negative selection, $CD4^+$ T cells generally become restricted to major histocompatibility complex (MHC) class II molecules and $CD8^+$ T cells to MHC class I molecules. These $CD8^+$ or $CD8^+$ T cells enter the periphery, where, after encountering antigen, they might be induced to become effector cells or long-lived memory cells.

The recognition of antigen and self-MHC is largely carried out by clonotypic $\alpha\beta$ T-cell receptors (TCR), present on the surface of T-lymphocytes in association with the CD3 complex. Like the immunoglobulins, TCR $\alpha$ and $\beta$ chains are assembled by somatic recombination of discontinuous germline gene segments during development. The generation of a highly diverse repertoire of human $\alpha\beta$ TCRs is accomplished by the recombination of a single V gene segment (selected from a pool of approximately 100 V$\alpha$s and 80 V$\beta$s) to an individual J gene segment (out of approximately 100 J$\alpha$s and 13 J$\beta$s). Template-independent nucleotide (N-segment) insertions at the junctions, D$\beta$ usage, and the imprecise joining of the germline gene segments further increase TCR diversity. Lai et al, *Adv. Immunol*, 46:1 (1989); Davis et al, *Nature*, 334:395 (1988). A dominant usage of certain V$\beta$ gene families in normal human peripheral T cells has been demonstrated. Choi et al, *Proc. Natl. Acad. Sci. USA*, 86:8941 (1989). A differential usage of specific $\alpha/\beta$ genes between $CD4^+$ and $CD8^+$ T peripheral T lymphocytes has also been found. Kisielow et al, *Nature*, 333:742 (1988).

In autoimmune diseases, T cells are believed to act as causative agents that incorrectly recognize the host body as foreign. In the autoimmune disease rheumatoid arthritis (RA) the local site of tissue injury is the joint. Joint pathology, characterized by inflammation and joint destruction, is the result of a complex interaction of cellular elements (inflammatory cells, immunocompetent cells and synovial lining cells) and their secreted products (Zvaifler, *Am. J. Med.*, 75:3 (1983)). The synovial tissue (pannus) in RA has the appearance of a hypercellular lymphoid organ in which the predominant lymphocytes are T cells, which make up 80% of the synovial tissue lymphocytes (Bankhurst et al, *Arth. Rheum.*, 19:555 (1976); Kurosaka, *J. Exp. Med.*, 158:1191 (1983)). In addition to the preponderance of T cells in the synovial pannus and an increased number of these T cells being activated in vivo, evidence for defects in T cell function and proportions have been described. Importantly, therapeutic measures that alter T cell function, such as total nodal lymphoid irradiation, significantly improve the clinical disease state but are associated with marked toxicity (Kotzin et al, *N. Engl. J. Med.*, 305:969 (1981)).

The relative risk of RA is high in individuals who inherit certain major histocompatibility complex genes. HLA DR4 and HLA DR1, for example, are present in more than 90% of adult rheumatoid arthritis patients. While the molecular basis for this genetic predisposition is unknown, because the major function of the MHC is to present processed antigens to T lymphocytes, it has been hypothesized that an environmental antigen or infection initiates an MHC-restricted immune response mediated at least initially by T cells in RA.

For many of these reasons, scientific investigators searching for the causative agent of rheumatoid arthritis have postulated that immune dysregulation associated with the disease may be associated with clonally expanded T cells detectable as a skewing of the peripheral $\alpha\beta$ T cell antigen receptor repertoire. U.S. Pat. No. 4,886,743, for example, describes methods for diagnosing autoimmune diseases, including rheumatoid arthritis, based upon an expansion of V $\beta$ gene usage in the total population of T lymphocytes in RA patients. PCT International Publication No. 90/06758, which broadly covers monoclonal antibodies reactive with epitopes on the T cell antigen receptor that can be used in the diagnosis and treatment of many immune-related diseases, associates rheumatoid arthritis with an increased percentage of T cells which express V$\delta$1, V$\Delta$3, V$\Delta$9, or V$\Delta$10 T cell receptor variable regions in a patient sample. Methods of diagnosing and treating RA patients with monoclonal antibodies specific for these gene products are described.

Despite the foregoing discoveries, investigators in the field of autoimmune disease pathology continue to seek correlations between the T cell antigen receptor and this chronic disease that could form the basis for future diagnostic and therapeutic modalities.

It is therefore an object of the present invention to provide a strong correlation between a variable region of the alpha chain of the T cell antigen receptor and rheumatoid arthritis.

Another object of the invention is to provide diagnostic methods and compositions for diagnosing and monitoring the progression of rheumatoid arthritis in a distinct subpopulation of RA patients.

A still further object of the invention is to provide therapeutic methods and compositions for treating a distinct subpopulation of individuals with RA.

SUMMARY OF THE INVENTION

These as well as other objects and advantages are achieved in accordance with the present invention, which provides monoclonal antibodies reactive with an epitope of the T cell receptor alpha chain variable region, Vαb 12.1, on human T lymphocytes. The monoclonal antibodies of the invention are reactive with approximately 2% of CD4$^+$ T lymphocytes and approximately 5% of CD8$^+$ T lymphocytes in peripheral blood cells in normal individuals, as determined, for example, by cytofluorographic analyses, and define a subset of individuals afflicted with an autoimmune disease, especially rheumatoid arthritis, that exhibit increased expression of the Vα12.1 gene product on CD8$^+$ T peripheral blood T lymphocytes when compared to normal individuals. Also provided are derivatives or fragments of the anti-Vα12.1 monoclonal antibodies reactive with the Vα12.1 variable region of the alpha chain of a T cell antigen receptor.

In another embodiment, the present invention provides a method for diagnosing a subset of individuals afflicted with an autoimmune disease, especially rheumatoid arthritis, by detecting an increase in the number of CD8$^+$ T cells in a sample that express the Vα12.1 gene product. The diagnostic method comprises (A) contacting a suitable sample containing T lymphocytes obtained from a patient suspected of having an autoimmune disease with a Vα12.1-specific reagent capable of binding to a cellular component of T cells and detecting Vα12.1 gene usage; (B) detecting the binding of the reagent and determining the number of CD8$^+$ T lymphocytes expressing Vα12.1; and (C) comparing the number of CD8$^+$ T lymphocytes as determined in step (B) with the number of CD8$^+$ T lymphocytes expressing Vα12.1 in a baseline sample, for example, a test sample from normal individuals that do not have the immune system disorder, to determine whether the number of CD8$^+$ T cells expressing the Vα12.1 gene is elevated in the subject suspected of having the disease relative to the number of CD8$^+$ T cells expressing the sequence in a normal subject. In one embodiment, the reagent is a monoclonal antibody or derivative or fragment thereof, reactive with an epitope of the Vα12.1 gene product.

A higher level of assurance can be made in the diagnosis of rheumatoid arthritis by establishing that the expansion of Vα12.1 gene usage is a clonal or oligoclonal expansion and by establishing that the Vα12.1 expansion correlates with the occurrence of the MHC allele, HLA-DQw2, in the Vα12.1-elevated patient population.

Diagnostic kits are also provided and comprise in packaged combinations a reagent, which can be a monoclonal antibody or fragment, capable of binding to T cells and detecting the presence of Vα12.1, or a labeled derivative of the reagent.

In another embodiment, rheumatoid arthritis can be treated by administering a therapeutically effective amount of a Vα12.1-specific reagent alone, or conjugated to a cytotoxic reagent.

The invention also provides for therapeutic compositions comprising the monoclonal antibodies of the invention.

DETAILED DESCRIPTION OF THE INVENTION

Figure 1:
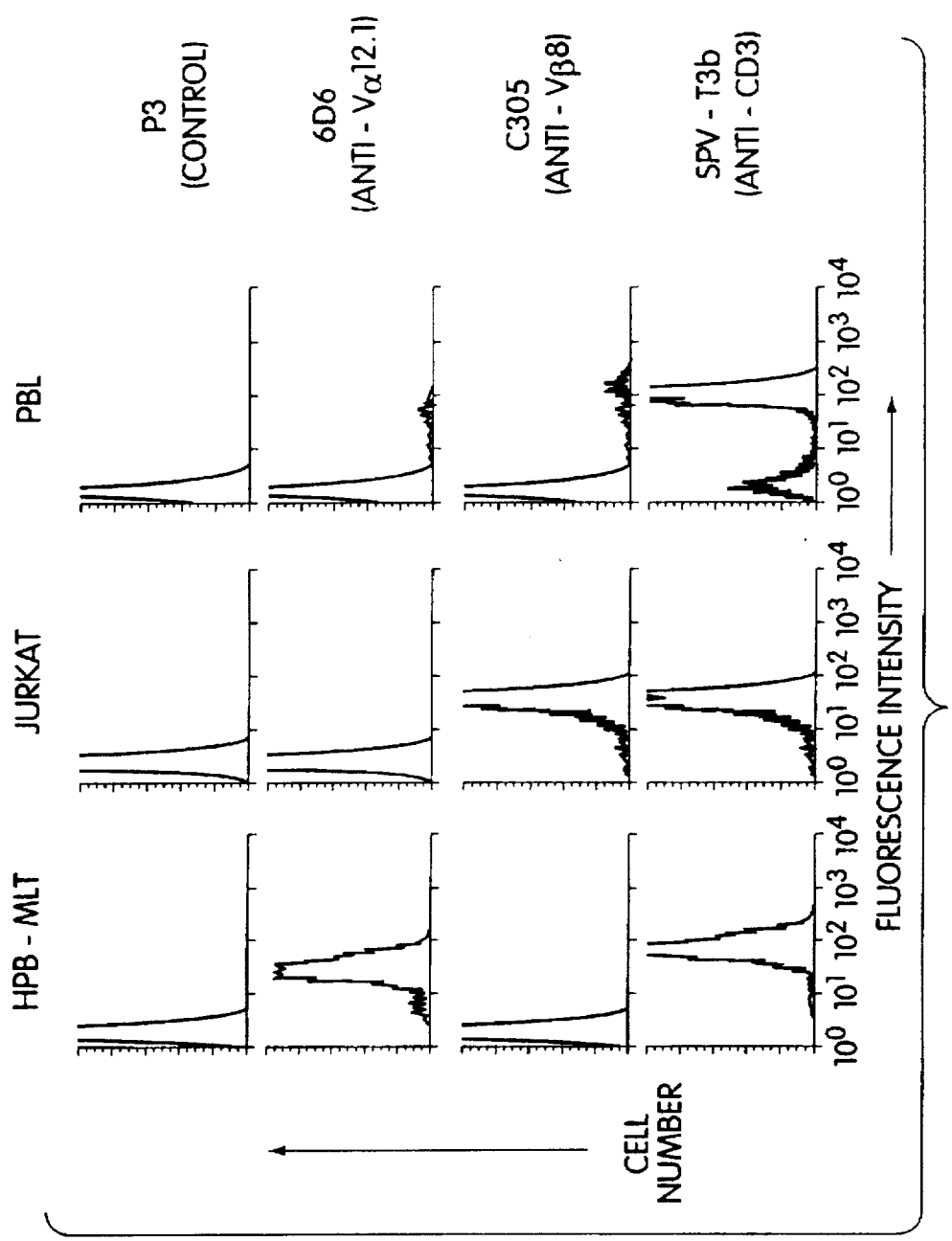
FIG. 1 shows the fluorescence pattern obtained on the FACSCAN flow cytometer (Becton Dickinson) after reacting cells from the leukemia cell line HPB-MLT, peripheral blood cells from a normal healthy patient, and leukemia cells from the Jurkat leukemia cell line, with the monoclonal antibody 6D6, specifically reactive with the Vα12.1 gene product. As illustrated by the fluorescent patterns, mAb 6D6 stained HPB-MLT cells and a minor subpopulation (2-5%) of peripheral lymphocytes but not the Jurkat T leukemia cell line. Staining of Jurkat cells and PBL with the Vβ 8-specific mAb C305 is shown for comparison. Isotype matched mAb P3 was used as a negative control and mAb T3b (anti-CD3) was used as positive control.

The present invention is directed to monoclonal antibodies that recognize an epitope of the $V\alpha 12.1$ variable region of the T cell antigen receptor and to methods of diagnosing, treating, and monitoring the progression of rheumatoid arthritis in a subpopulation of RA patients that exhibit a clonal or oligoclonal expansion of peripheral blood T cells expressing $V\alpha 12.1$ using $V\alpha 12.1$-specific reagents.

As used herein, the phrase "$V\alpha 12.1$-specific reagent" means a reagent that is capable of binding to a cellular component of T lymphocytes and detecting the T cell receptor $V\alpha 12.1$ variable region gene or gene product thereof. Such reagents include nucleic acid sequences or probes that can hybridize to nucleic acid sequences within the $V\alpha 12.1$ gene itself and to antibodies that bind to an epitope of the $V\alpha 12.1$ gene product on T cells for diagnosis and monitoring of the disease process and also include antibodies for treatment of a subpopulation of RA patients exhibiting an expansion of $V\alpha 12.1$ gene usage.

In the following description, reference will be made to various methodologies known to those of skill in the art of immunology, cell biology, and molecular biology. Publications and other materials setting forth such known methodologies to which reference is made are incorporated herein by reference in their entireties as though set forth in full.

1. Antibodies Of The Invention

The present invention is directed to an antibody or fragment or derivative thereof, specific for an epitope of the $V\alpha 12.1$ variable region of the T cell antigen receptor. The antibodies of the invention are useful in diagnosis and therapy of an autoimmune disease, preferably rheumatoid arthritis (RA) The term "antibody" is meant to include polyclonal antibodies, monoclonal antibodies, (mAbs) chimaeric, and humanized antibodies (see below). Monoclonal antibodies, and chimaeric and humanized antibodies, are preferred for diagnosis and therapy, respectively.

A $V\alpha 12.1$-specific monoclonal antibody of the present invention, designated 6D6, enabled the analysis of the expression of the $V\alpha 12.1$ gene product in peripheral blood T cell subsets of normal, healthy human subjects by flow cytometry. The results of this analysis revealed that approximately 2% of $CD4^+$ peripheral blood lymphocytes express the $V\alpha 12.1$ gene product, while about 5% of $CD8^+$ T peripheral blood lymphocytes express $V\alpha 12.1$. When expression of $V\alpha 12.1$ was examined in patients with several autoimmune diseases, a marked expansion of $V\alpha 12.1$ in the $CD8^+$ T peripheral blood T cells of a subset of rheumatoid arthritis patients was detected.

In accordance with the present invention, all of the teachings and procedures described herein with respect to 6D6 can be used by persons skilled in this area of technology to develop other antibodies specifically reactive with an epitope of $V\alpha 12.1$.

a. Preparation of Monoclonal Antibodies

The monoclonal antibodies of the invention can be prepared by using any technique that provides for the production of antibody molecules by continuous cell lines in culture. These include, but are not limited to, the original techniques of Köhler and Milstein, *Nature*, 265:495–497 (1975), modified as described in Brenner et al, *J. Immunol.*, 138:1502 (1987), the pertinent portions of which are hereby incorporated by reference and the more recent human B cell hybridoma technique, EBV-hybridoma technique, and trioma techniques well known to persons skilled in the art.

As part of the production of the monoclonal antibodies of the invention, various host animals, including but not limited to rabbits, mice, hamsters, and rats can be immunized by injection with purified T cell antigen receptors or polypeptides or fragments thereof, a recombinant or synthetic version thereof, or T lymphocytes.

In generating the monoclonal antibodies of the present invention, any cell line that uses the Vα12.1 gene can be used in the immunization procedure. An example of human T cell line known to use Vα12.1 is the HPB MLT human leukemia cell line (Sim et al, *Nature*, 312:771 (December 1984)). Whole T cells naturally expressing Vα12.1, such as HPB-MLT, as well as partially purified T cell receptors can be employed as immunogens to generate monoclonal antibodies specific to the variable region of the alpha chain. As an example, partially purified T cell receptor complexes isolated from the human T cell leukemia cell line HPB-MLT can be used as the immunogen. Preferably, T cell receptor complexes are partially purified by immunoprecipitation using anti-CD3 mAb adsorbed to Protein A bearing fixed *Staphylococcus aureus* bacteria (Pansorbin, Calbiochem, San Diego, Calif.) using the protocol previously described, *J. Immunol.*, 138: 1502 (1987), although any suitable method for partially purifying the T cell receptor for antigen from whole T cells can satisfactorily be employed. Alternative methods of partial purification will be readily apparent to persons skilled in this area of technology.

Whole cells that can be used as the immunogens to produce Vα12.1-specific monoclonal antibodies also include recombinant transfectants that express TCR including Vα12.1. In a particularly preferred embodiment, human Vα12.1 is transfected into suitable cells from another species such that the human Vα12.1 gene product is expressed on the cell surface in combination with the T cell receptor from another species. As an example, human Vα12.1 is transfected into a murine T-T hybridoma prepared from a murine T cell line, such as BW-1100.129 or BW-1100.125, which are defective in that they fail to express the α chain of the T cell receptor for antigen. These cell lines have been described by White et al in *Journal of Immunology*, 143:1822–1825 (September 1989) and are readily available. The transfectants thus-prepared are then used in the immunization procedure. This procedure is described by Choi et al, *Nature*, 346:471 (August 1990), the pertinent portions of which are incorporated by reference, and has as an advantage increasing the efficiency of an effective immune response to the human antigen. The cDNA sequence for Vα12.1 is known (Sim et al, *Nature*, 312:771 (1984)) and can readily be prepared for transfection by persons skilled in the art for generation of monoclonal antibodies in accordance with the teachings and procedures herein described.

Other Vα12.1 TCR-containing samples that can be used in the immunization protocol include peptide sequences that correspond to Vα12.1 and recombinantly expressed and purified proteins produced from expression systems.

Samples of the whole T cells, partially purified T cell receptor protein or other suitable immunogen can then be injected into a host animal, for example a mouse and, after a sufficient time, the animal is sacrificed and spleen or other immune cells obtained. The spleen or other immune cells are immortalized by fusing the spleen cells with an immortalized cell line, generally in the presence of a fusion enhancing reagent, for example, polyethylene glycol. The resulting cells, which include the fused hybridomas, are then allowed to grow in a selective medium, such as HAT medium, and the surviving cells are grown in such medium using limiting dilution conditions. The cells are grown in a suitable container, e.g., microtiter wells, and the supernatant is screened for monoclonal antibodies having the desired specificity.

In a preferred embodiment, the monoclonal antibodies of the present invention are prepared substantially as follows. About $5 \times 10^6$ whole HPB-MLT cells are injected intraperitoneally into 8 week old Balb/c mice in complete Freund's adjuvant. Four to five more intraperitoneal immunizations are conducted at two to three week intervals, also with about $5 \times 10^6$ HPB-MLT cells in incomplete Freund's. The final boost is made intravenously into the tail vein, without adjuvant. The mice are sacrificed about three days following the final boost and spleens removed. The immune spleen cells are then removed and fused with an appropriate myeloma cell line, such as P3X63Ag8.653, in the presence of polyethylene glycol in accordance with standard techniques.

Screening procedures that can be used to screen hybridoma cells expressing anti-Vα12.1 monoclonal antibody include but are not limited to (1) enzyme-linked immunoadsorbent assays (ELISA), (2) immunoprecipitation and (3) fluorescent activated cell sorter (FACS) analyses. Many different ELISAS that can be used to screen for anti-Vα12.1 monoclonal antibodies can be envisioned by persons skilled in the art. These include but are not limited to formats comprising purified, synthesized or recombinantly expressed Vα12.1 polypeptide attached to a solid phase or formats comprising the use of whole T cells or cell lysate membrane preparations either attached to the solid phase or bound to antibodies attached to the solid phase. Samples of hybridoma supernatants would be reacted with either of these two formats, followed by incubation with, for instance, goat-anti-mouse immunoglobulin complexed to an enzyme-substrate that can be visually identified.

Where the immunogen comprises whole T cells or T cells transfected with human Vα12.1-containing TCR, screening is preferably conducted using human HBP-MLT in a FACS analysis.

It is also possible to screen antibodies for their ability to immunoprecipitate a known Vα12.1 as analyzed by SDS-polyacrylamide gel electrophoresis or Western blot analysis.

After initial screening, further characterization of the hybridomas for those that secrete monoclonal antibody specific for the Vα12.1 gene product can be accomplished substantially as described in the Examples herein. Monoclonal antibodies specific for an epitope of Vα12.1 will have the same TCR chain specificity as 6D6, as determined, for example, by immunoprecipitation using a cell line known to express Vα12.1. Monoclonal antibodies that compete with 6D6 in competition assays well known to persons skilled in the art are likely to recognize essentially the same epitope as 6D6, while monoclonal antibodies that fail to compete are likely to recognize a different epitope of the Vα12.1 gene product. The specificity of the monoclonal antibody for a Vα12.1 sequence can be confirmed by cloning, hybridization and sequencing techniques, as described in Example 1. Additional confirmatory analyses which can be conducted include preclearing and/or cross-blocking techniques well known to persons skilled in the art.

A molecular clone containing a DNA sequence of an antibody to an epitope of Vα12.1 can be prepared by known techniques. (See, e.g., Sambrook, Fritsch and Maniatis, Molecular Cloning, A Laboratory Manual, Cold Spring Harbor Laboratory, Cold Spring Harbor, N.Y. (1989)). Recombinant DNA methodology may be used to construct nucleic acid sequences which encode a monoclonal antibody molecule or antigen binding region thereof.

Once the desired hybridoma has been selected and cloned, the resultant antibody may be produced in one of two major ways. The purest monoclonal antibody is produced by in vitro culturing of the desired hybridoma in a suitable medium for a suitable length of time, followed by the recovery of the desired antibody from the supernatant. The length of time and medium are known or can readily be determined. This in vitro technique produces essentially monospecific monoclonal antibody, essentially free from other species of anti-human immunoglobulin. However, the in vitro method may not produce a sufficient quantity or concentration of antibody for some purposes, since the quantity of antibody generated is only about 50 μg/ml.

To produce a much larger quantity of monoclonal antibody, the desired hybridoma may be injected into an animal, such as a mouse. Preferably the mice are syngeneic or semi-syngeneic to the strain from which the monoclonal-antibody producing hybridomas were obtained. Injection of the hybridoma causes formation of antibody producing tumors after a suitable incubation time, which will result in a high concentration of the desired antibody (about 5–20 mg/ml) in the ascites of the host animal.

Antibody molecules can be purified by known techniques, e.g. by immunoabsorption or immunoaffinity chromatography, chromatographic methods such as high performance liquid chromatography or a combination thereof.

Following these protocols, any person skilled in this area of technology can readily isolate hybrid cell lines which secrete a monoclonal antibody exhibiting specificity for an epitope of Vα12.1. Although only a single hybridoma producing a monoclonal antibody against human Vα12.1 antigen is exemplified by way of working example, it is contemplated that the present invention encompasses all monoclonal antibodies exhibiting the characteristics described herein. For example, it was determined by immunodiffusion that the subject antibody (6D6) belongs to the subclass $IgG_1$, which is one of four subclasses of murine IgG. These subclasses of immunoglobulin G differ from one another in the so-called "fixed" regions, although an antibody to a specific antigen will have a so-called "variable" region which is functionally identical regardless of which subclass of immunoglobulin G it belongs to. That is, a monoclonal antibody exhibiting the characteristic described herein may be of subclass $IgG_1$, $IgG_2a$, $IgG_2b$, or $IgG_3$, or of classes IgM, IgA, or other known Ig classes. The differences among these classes or subclasses will not affect the selectivity of the reaction pattern of the antibody, but may affect the further reaction of the antibody with other materials, such as (for example) complement or anti-mouse-antibodies. Although the subject antibody is specifically $IgG_1$, it is contemplated that antibodies having the patterns of reactivity illustrated herein are included within the subject invention regardless of the immunoglobulin class or subclass to which they belong.

Moreover, while the specific example of the novel antibody of the present invention is from a murine source, this is not meant to be a limitation. The above antibody and those antibodies having the characteristics of the 6D6 antibody, whether from a murine source, other mammalian source including human, rat, or other sources, or combinations thereof, are included within the scope of this invention, as set forth above.

b. Preparation of Fragments and Derivatives of Antibodies
Molecular Fragments and Derivatives Also included within the scope of the present invention are antibody fragments and derivatives which comprise at least the functional portion of the antigen binding domain of the anti-Vα12.1 antibody molecule.

Antibody fragments which contain the binding domain of the molecule can be generated by known techniques. For example, such fragments include, but are not limited to: the F(ab')₂ fragment which can be produced by pepsin digestion of the antibody molecule; the Fab' fragments which can be generated by reducing the disulfide bridges of the F(ab')₂ fragment, and the Fab fragments which can be generated by treating the antibody molecule with papain and a reducing agent. See, e.g., National Institutes of Health, 1 *Current Protocols In Immunology*, Coligan et al., ed. §§2.8, 2.10 (Wiley Interscience, 1991).

Antibody fragments also include Fv fragments, i.e., antibody products in which there are no constant region amino acid residues. Such fragments can be produced, for example as described in WO 92/04381 or U.S. Pat. No. 4,642,334.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimaeric antibody derivatives, i.e. antibody molecules that combine a non-human animal variable region and a human constant region. Chimaeric antibody molecules can include, for example, the antigen binding domain from an antibody of a mouse, rat, or other species, with human constant regions. A variety of approaches for making chimaeric antibodies have been described and can be used to make chimaeric antibodies containing the immunoglobulin variable region which recognize the gene product of Vα-12.1. See, for example, Morrison et al., *Proc. Natl. Acad. Sci. U.S.A.* 81:6851 (1985); Takeda et al., *Nature* 314:452 (1985), Cabilly et al., U.S. Pat. No. 4,816,567; Boss et al. U.S. Pat. No. 4,816,397; Tanaguchi et al., Eur. Patent Pub. EP171496; Eur. Patent Pub. 0173494; United Kingdom Patent GB 2177096B. Such chimaeras produce a less marked immune response than non-chimaeric antibodies.

For human therapeutic purposes, the Vα12.1-specific monoclonal or chimaeric antibodies can be further humanized by producing human constant region chimaeras, in which even parts of the variable regions, especially the conserved or framework regions of the antigen-binding domain, are of human origin and only the hypervariable regions are of non-human origin. Such altered immunoglobulin molecules may be made by any of several techniques known in the art, (e.g., Teng et al., *Proc. Natl. Acad. Sci. U.S.A.*, 80:7308–7312 (1983); Kozbor et al., *Immunology Today*, 4:7279 (1983); Olsson et al., *Meth. Enzymol.*, 92:3–16 (1982)), and are preferably made according to the teachings of PCT Pub. WO 92/06193 or EP 0239400. There are also a number of companies that humanize antibodies commercially, for example Scotgen Limited, 2 Holly Road, Twickenham, Middlesex, Great Britain.

These humanized antibodies are preferable for immunotherapy in that they minimize the effects of an immune response. This in turn leads to a lowering of any concomitant immunosuppression and to include increased long term effectiveness in, for instance, chronic disease situations or situations requiring repeated antibody treatments.

Chemical and Biological Derivatives For Diagnosis and Therapy

In addition to molecular antibody fragments and derivatives, antibody derivatives or immunoconjugates consisting of an antibody molecule or binding region thereof bound to a label such as a radioisotope, flourescein, enzyme, or other tracer molecule can be made by techniques known in the art. Alternatively, the antibody molecule or fragment thereof can be bound to a therapeutically useful biological or chemical molecule targeted to its desired site of action by virtue of the antibody's binding specificity. As one example of such an embodiment, a cytotoxic compound can be conjugated to an antibody of the invention which is specific for Vα12.1$^+$ lymphocytes which are the causative agents of an autoimmune disorder. The cytotoxic compound, which can be for example, a radionucleotide or a toxin, such as a diphtheria toxin, in conjugated form is thus targeted to the implicated T lymphocytes.

c. Antibody Isotype

In addition to the properties described supra, the isotype of the anti-Vα12.1-specific antibody is also important. For different clinical applications, an antibody of a specific isotype may be preferable to one of a different isotype. For example, the IgG2a isotype reacts with Fc receptors on cells of the reticuloendothelial system and is more readily removed from the circulation and sequestered in the spleen than other isotypes. Such an antibody that has reacted with a target cell may result in the more efficient removal of the target cell from the site of active disease. In addition, some isotypes (such as IgG2a) are more effective in antibody dependent cell cytotoxicity reactions than others. In general, antibodies of the IgG isotype are preferable to those of the IgM isotype because they have higher binding affinities.

The desired isotype of an antibody may be selected by screening potential antibodies by an ELISA assay designed to select the isotype of interest. For example, the solid phase can be coated with goat anti-mouse IgG Fc specific antibodies, if it is desired to select for antibodies having the IgG isotype.

Given an antibody of one isotype, it is also possible to switch the isotype to a different isotype. Many methods for accomplishing this switch are known to those skilled in the art. For example, the isotype switch can be done by repeatedly selecting for the isotype of interest using magnetic beads (super paramagnetic iron oxide particles, Biomag$^c$ beads purchased from Advanced Magnetics, Inc.) coated with a goat anti-mouse antibody preparation including all isotype classes. In switching the isotype from IgG1 to Igg2a, for instance, the IgG2a binding sites on the coated magnetic beads are first blocked with an irrelevant antibody of the IgG2a isotype. All cells producing antibodies of differing isotypes will then be bound by the beads and removed magnetically, resulting in an enrichment of cells producing the IgG2a isotype. These cells can then be cloned by limiting dilution, and using commercially available anti-isotypic reagents in an ELISA assay, the IgG2a producing clones can be identified. A method which facilitates selecting for the isotype of interest is exemplified in PCT International Publication No. WO 90/06758.

d. Immunoassays

The antibodies of the invention and the fragments and derivatives thereof containing the binding region (e.g., Fab, Fab', F(ab')$_2$), can be used in various immunoassays. Such immunoassays include, but are not limited to, competitive and non-competitive assay systems using techniques such as radioimmunoassays, ELISA (enzyme linked immunosorbent assay), "sandwich" immunoassays, precipitin reactions, gel diffusion precipitin reactions, immunodiffusion assays, agglutination assays, complement fixation assays, immunoradiometric assays, fluorescent immunoassays, protein A immunoassays, and immunoelectrophoresis assays, to name but a few.

2. Diagnosing Rheumatoid Arthritis With Vα12.1-Specific Reagents

The monoclonal antibodies, fragments, and derivatives thereof of the present invention, as well as other Vα12.1-specific reagents, are useful for studying the T cell receptor repertoire in a variety of immune disorders and are particularly useful in diagnosing and/or monitoring the disease process in a subset of human patients afflicted with rheumatoid arthritis. Thus, in one embodiment of the invention rheumatoid arthritis is diagnosed and monitored by detecting the specific binding of a reagent having specificity for a cellular T cell component that is indicative of the presence and usage of the Vα12.1 gene.

a. Antibodies

In a particularly preferred embodiment, the reagent is a monoclonal antibody or fragment or derivative thereof, reactive with an epitope of the Vα12.1 gene product on CD8$^+$ T lymphocytes in a suitable patient sample. Rheumatoid arthritis is diagnosed by detecting increased expression of Vα12.1 on CD8$^+$ T cells in the patient sample when compared to a suitable base line sample, as, for example, a sample from a normal human subject that does not have the immune disease.

A suitable sample for diagnosis includes cells from essentially any body fluid, including but not limited to peripheral blood, plasma, lymphatic fluid, and synovial fluid, to name just a few. Alternatively a tissue sample, such as synovial membrane, from the site of suspected injury may be obtained by biopsy and subjected to testing. In a particularly preferred embodiment of the invention, rheumatoid arthritis is diagnosed by detecting elevated numbers of Vα12.1 positive cells on CD8$^+$ T lymphocytes from peripheral blood relative to the population of Vα12.1 positive CD8$^+$ T cells in normal individuals.

A diagnostic method in accordance with the present invention involves contacting the sample containing T cells obtained from a subject suspected of having an autoimmune disease, such as rheumatoid arthritis, with a monoclonal antibody or fragment or derivative thereof specific for an epitope of the Vα12.1 gene product on T cells, detecting the binding of antibodies to the Vα12.1 gene product on the T cells and determining the number of CD8$^+$ T cells expressing the Vα12.1 gene product. The results are then compared to the number of CD8$^+$ T lymphocytes thus determined as expressing the Vα12.1 gene product with the number of CD8$^+$ T cells expressing the Vα12.1 gene product determined for a normal subject. The presence of an increased number of CD8$^+$ T cells expressing the Vα12.1 gene product relative to the number of Vα12.1$^+$CD8$^+$ T cells of a normal subject is diagnostic for a subset of patients with the disease. In accordance with the present invention, the number of CD8$^+$ T cells expressing the Vα12.1 gene product can be determined either qualitatively or quantitatively.

When used in a diagnostic assay as described, the antibody is typically labeled so that its binding with the T cell receptor can be detected. Any suitable label well known to persons skilled in the art, including but not limited to fluorescent dyes, radioactive isotopes, enzymes which catalyze a reaction producing detectable products, biotin, or metal ions detectable by nuclear magnetic resonance can be employed.

Binding of the monoclonal antibodies may be accomplished in vivo or in vitro.

In vitro binding may be performed using histological specimens or subfractions of tissue or fluid, i.e., substantially purified T cells. For preparation of lymphocytes from a sample of peripheral blood for in vitro binding, mononuclear cells are separated from the rest of the blood. For example, peripheral blood is anticoagulated with heparin, diluted with an equal volume of phosphate buffered saline and subjected to density gradient centrifugation, thereby separating the mononuclear cells (primarily lymphocytes) from the rest of the blood. The cells are then washed in buffer and suspended in buffer with a small amount, e.g., 0.01–1%, preferably about 0.1%, gelatin and a small amount, e.g., 0.01–1%, preferably about 0.1%, sodium azide at $5\times10^6$ per ml. Alternatively, separation of the white blood cells can be achieved by whole blood hemolysis.

Cryostat sections from tissue obtained from biopsy are prepared by cutting the tissue into thin sections, preferably about 6 μm thick, at about −25° C. and then allowing the sections to dry at room temperature.

The thus-obtained mononuclear cells or cryostat sections are then subjected to an assay that enables the determination of the number of $CD8^+$ T cells that express $V\alpha12.1$ in the sample. Detection of $CD8^+$ T lymphocytes in a population and those which are $V\alpha12.1$ positive can be determined simultaneously, or sequentially. The $CD8^+$ T subpopulation of T cells can be isolated from other mononuclear cells by removing the $CD8^+$ subpopulation or alternatively, by enriching for the $CD8^+$ cells. The latter may be accomplished, for example, by reacting cells with an anti-CD8 monoclonal antibody and capturing such cells on beads coated with anti-immunoglobulin. Identification of the $CD8^+$ subpopulation can be accomplished using, for example, a monoclonal antibody specific for the CD8 cell surface antigen, such as OKT8 (Ortho Pharmaceuticals, Raritan, N.J.).

In vivo binding may be achieved by administering the antibody or fragment or derivative by any means known in the art (including but not limited to intravenous, intraperitoneal, intranasal, and intraarterial, to name but a few) such that immunospecific binding may be detected; for example, by attaching a radioactive label to the diagnostic antibody, fragment, or derivative.

b. Nucleic Acids

In another embodiment of the invention, an autoimmune disorder, such as RA, is diagnosed by using nucleic acid sequences that detect the presence of $V\alpha12.1$ DNA or RNA, derived from $CD8^+$ T lymphocytes. Depending on the technique to be used, either DNA or RNA probes containing $V\alpha12.1$ sequences can be used to diagnose a subset of rheumatoid arthritis patients. The DNA sequences for the $V\alpha12.1$ gene are known and this information can readily be used by persons skilled in the art to design diagnostic tests to detect the $V\alpha12.1$ elevation described herein. For sequence information, see, Sim et al., *Nature*, 312:771–775 (December, 1984), the pertinent portions of which are hereby incorporated by reference. Samples from patients suspected of having RA can be analyzed for the expansions of $V\alpha12.1^+$ T cells by cDNA synthesis and polymerase chain reaction amplification, using $V\alpha12.1$-TCA-specific oligonucleotide primers. Slot blot hybridization procedure can be used to quantitate the relative amounts of $V\alpha12.1$ containing $CD8^+$ T cells. This procedure, sometimes referred to as quantitative polymerase chain reaction, is exemplified in PCT International Publication W090/06758.

Briefly, the first step is to isolate the messenger RNA from $CD8^+$ cells from a patient sample. First strand cDNA is then synthesized using a virus reverse transcriptase in the presence of an oligo- (dT) primer, essentially according to published procedures (Okayama and Berg, *Mol. Cell Biol.*, 2:161–170 (1982).

Polymerase chain reaction is then carried out in accordance with established techniques using primers based on published sequences (e.g., $V.\alpha12.1$ and $C\alpha$-specific primers). The PCR products are then size fractionated, transferred, and hybridized with internal region radiolabeled probes on a slot blot apparatus. Following hybridization and washing, blots are dried and radiocavity counted.

The results are compared to blots obtained from $CD8^+$ derived cDNA from a normal subject that does not have the immune disorder to determine whether $V\alpha12.1$ gene usage in expanded in the patient suspected of having RA.

An increased percentage of $CD8^+$ T cells expressing $V\alpha12.1$, as evidenced by an increased intensity on the autoradiograph, is diagnostic for RA.

While the foregoing illustrates a preferred method for using nucleic acid probes as reagents in the diagnostic assay of the invention, other techniques including Southern hybridizations will be appreciated by persons skilled in the art and are considered within the spirit and scope of the invention.

3. Confirmatory Diagnostic Procedures

It should be understood that the diagnostic methods of the invention are best used in the context of other diagnostic parameters in order to obtain a comprehensive patient diagnosis. A higher level of assurance can be made in the diagnosis of RA by determining whether the expansion of $V\alpha12.1$ in a patient suspected of having the immune disorder is a clonal or oligoclonal, as opposed to a polyclonal, expansion. A clonal or oligoclonal population of T cell receptors in patients exhibiting an expansion in $V\alpha12.1$ is indicative of an antigen-driven expansion and, in accordance with the present invention, is further diagnostic of RA.

As used herein, a clonal expansion is one in which there is one dominant repeated sequence including $V\alpha12.1$ and no other repeated $V\alpha12.1$-containing sequences. An oligoclonal expansion may include as many as 2–6 different repeated $V\alpha12.1$-containing sequences, while, in a polyclonal expansion, virtually every sequence obtained is different from the other sequences, with only rare repeated sequences being noted. In the case where the expansion of $V\alpha12.1^+$ T cells is a clonal or oligoclonal one, there may also be an indeterminate number of distinct sequences present. There are a number of techniques well known to persons skilled in the art that can be used to detect a clonal expansion, including 1) polymerase chain reaction amplification of cDNA from a suitable patient sample followed by sequencing and 2) Southern blot hybridization. Direct and inverse PCR reactions can be used, as described in the Examples. Preferably, the nucleic acid samples used for the clonality analyses are obtained from an enriched CD8+ population of the patient's peripheral blood lymphocytes.

Southern hybridization is the preferred procedure for detecting clonality of the $V\alpha12.1$ expansion when screening a large number of patients suspected of having RA. When only a small number of patients is involved, polymerase chain reaction followed by sequencing is the preferred technique for determining whether the expansion of $V\alpha12.1$ is clonal or oligoclonal. An example of this technique for determining clonality in a patient sample is provided in the Examples herein.

A higher level of assurance can also be made in the diagnosis of RA through HLA-typing. In accordance with the present invention, it has been discovered that the subpopulation of RA patients exhibiting elevated $V\alpha12.1$ expression also exhibit a statistically significant increase in the proportion of occurrence of the HLA-DQw2 allele. Association of the HLA-DQw2 genotype with an elevation in $V\alpha12.1$ bearing $CD8^+$ T cells is diagnostic for a subset of patients with RA. HLA-typing is widely known and used and can be conducted in accordance with any of the known techniques, including serological detection and detection of HLA-DR locus gene products by cellular techniques. See generally, Tait and Simmons, *Detection of Immune-Associated Genetic Markers of Human Disease*, Chapter 4, (Churchill and Livingston, pub., 1984).

In addition, a diagnosis of rheumatoid arthritis may be made based on the methods of the invention in the context of other clinical features of rheumatoid arthritis, such as typical joint involvement (chronic, symmetrical arthritis; early involvement most often in the hands); characteristic radiographic features; the presence of rheumatoid factor; the presence of rheumatoid nodules, etc. (Fishman et al., Medicine, Second Edition, J.B. Lippincott Company, Philadelphia, pp. 340–346). As with any diagnostic criteria, the parameters disclosed in the present invention may not be sole determinants, or pathognomonic, of a particular disorder.

4. Diagnostic Kits

Diagnostic kits are useful in performing the diagnostic methodology of the present invention. Such kits include a Vα12.1-specific reagent, preferably an anti-Vα12.1 monoclonal antibody of the invention, or a fragment or derivative thereof, coupled with an appropriate detectable marker for the analysis, suitable standards, solid phase components such as microscope slides, microtiter dishes, or beads, as necessary, and other components such as enzymes and substrates useful for detection. The diagnostic kits will also typically comprises a reagent capable of identifying the $CD8^+$ subpopulation of lymphocytes, preferably an anti-CD8 monoclonal antibody, together with the appropriate reagents and labels. The diagnostic kits of the present invention can also include HLA-typing reagents and particularly a reagent for detecting the HLA-DQw2 allele.

5. Treatment of Rheumatoid Arthritis With Anti-Vα12.1 Antibodies

In another embodiment of the invention, a Vα12.1-specific reagent is administered to a subject in order to modulate the function and number of $Vα12.1^+$ T cells in vivo. Preferably, the reagent is a monoclonal antibody, derivative, or fragment thereof specific for an epitope of the Vα12.1 variable region of the TCR, although other Vα12.1 specific reagents may alternatively be employed. Although it is contemplated that the Vα12.1 specific reagents will have applicability for animal subjects in addition to human beings, such as domesticated animals, the therapeutic aspects of the invention are of the greatest value in the treatment of rheumatoid arthritis in humans.

Modulation of Vα12.1 T cells in vivo using the Vα12.1-specific antibodies of the invention involves administering a single dose or multiple doses of the antibody, fragment, or derivative in a therapeutically effective amount. The modulation of the $Vα12.1^+$ T cell population can either be positive, resulting in an increased number and function of the Vα12.1 expanded population of T cells, or it can be negative, resulting in the elimination of the deleterious population of T cells. Thus, for example, if the antibody is capable of inducing in vitro T cell proliferation, and it is desirable to enhance the expanded $Vα12.1^+$ T cell population, the antibodies, fragments or derivatives may be administered in an unconjugated form to increase the Vα12.1 expanded population and stimulate specific cell-mediated immunity.

In most instances, however, it will be desirable to eliminate or block (i.e., negatively modulate) the Vα12.1 expanded T cell population. Therefore, in another particular embodiment, an antibody, fragment, or derivative specific for an epitope of the Vα12.1 variable region of the TCR can be used to target a cytotoxic molecule to $Vα12.1 CD8^+$ cells which are the causative agents of the autoimmune disorder, thereby negatively effecting the function and number of these T cells. It is also possible to use an unconjugated Vα12.1-specific antibody therapeutically to block the interaction of effector T cells with their specific antigen and thus modulate a deleterious response. A further therapeutic embodiment is to administer an antibody therapeutically to bind to its target and mark those cells for elimination by the RES system or by antibody dependent cell cytotoxicity (ADCC) reactions, with the ablation of the target T cells resulting in a therapeutic effect.

The $Vα12^+CD8^+$ T cells are auto reactive (i.e., self-reactive) (See FIGS. 6–11), which further indicates these cells are relevant as a target for treatment of rheumatoid arthritis (an autoimmune disease). FIGS. 12A and 12B illustrate that $CD8^+$ cells showed a high percentage of apoptotic cell death when contacted with a Vα12 specific antibody 6D6. In contrast, normal cells proliferate when exposed to the antibody. The clonally expanded $Vα12^+$ cells seen in rheumatoid arthritis patients are in the $CD8^+$ pool. These contrasting results further illustrate the deviant nature of these cells. Whereas the receptor binding of the normal cells by the antibodies may be beneficial or benign, this is not the case with binding of these $CD8^+$ cells. Accordingly, these results further confirm that these cells are an excellent target for therapy. These examples also show that the antibody per se can be used to preferentially kill $Vα12^+CD8^+$ cells compared with other $Vα12^+$ cells.

The route of administration for any of the foregoing therapeutic modalities may include intradermal, intramuscular, intraperitoneal, intravenous, or subcutaneous injection, intranasal routes and slow release forms, such as those delivered in transplantable forms, on patches or in other colloidal forms. In one embodiment, the antibody can be encapsulated in liposomes.

When used to treat disease, the Vα12.1-specific antibodies can be used in unmodified form for positively modulating the number and function of the Vα12.1 expanded T cell population or in unmodified form or conjugated to radioucleotides or toxins by means well known in the art and used to deliver the conjugated substance to deleterious T cells for negative modulation. The 6D6 monoclonal antibody is a preferred therapeutic antibody. Non-limiting examples of radionucleotides which can be conjugated to antibodies and administered include $^{212}Bi$, $^{131}I$, $^{186}Re$, and $^{90}Y$. These elements exert their effect by locally irradiating the cells, leading to various intracellular lesions, well known to persons skilled in the art of radiotherapy.

Cytotoxic drugs that can be conjugated to antibodies and administered for in vivo therapy include, but are not limited to, daunorubicin, doxorubicin, methotrexate, and mytomycin C. For a more detailed discussion of these classes of drugs and their mechanisms of action, see, Goodman et al., Goodman and Gilman's The Pharmaceutical Basis Of Therapeutics, 8th ed. Pergamon Press (1991).

As an example of conjugation to a toxin, the 6D6 monoclonal antibody can be combined with diphtheria toxin, by the method of Bumol, Proc. Natl. Acad. Sci., 80:529 (1983). Briefly, monoclonal antibodies reactive with the Vα12.1 T-cell receptor segment are prepared by as described. The antibodies are purified and combined with excess (6 mol/mol) N-succinimydyl 3-(2-pyridyldithio) propionate (Pharmacia, Uppsala, Sweden) in PBS. After 30 minutes incubation at room temperature, the solution is dialyzed against PBS. The modified antibodies are conjugated with an appropriate toxin, such as diphtheria toxin A chain. Other toxins such as ricin A can also be employed. The diphtheria toxin A chain is isolated as detailed in Bumol, supra. The modified antibodies are mixed with excess (3 mol/mol) reduced diphtheria toxin A chain (10% of the total volume), allowed to react for 36 hours at 40° C., and concentrated by chromatography on Sephadex G-2000. The product is applied to a Sephadex G200 column (1.0×100 cm), allowed to equilibrate and eluted with PBS.

The effective dose of the therapeutic reagent will be a function of the particular Vα12.1-specific reagent or fragment or derivative employed, the presence and nature of conjugated therapeutic reagent, the patient, and his or her clinical condition. Effective doses of the antibodies, fragments, or derivatives of the invention for use in preventing, suppressing, or treating an immune-related disease are in the range of about 1 ng to 100 mg/kg body weight. A preferred dosage range is between about 10 ng and 10 mg/kg, and a more preferred dosage range is between 100 ng and 1 mg/kg.

The mode of treatment of rheumatoid arthritis can involve acute treatment conditions, and will typically also involve chronic treatment conditions, given the nature of the disease. This in turn will lead to treatment regimens involving initial bolus administrations or continuous administrations, followed by repeated administrations at treatment intervals, initially approximately every three days, and later approximately every couple of weeks, as the severity of the disease decreases with the treatment.

Various pharmacologic compositions may be utilized in order to deliver the antibodies, or fragments or derivatives thereof, according to the invention. Any suitable pharmaceutical agent with desirable solubility characteristics and chemical properties may be used, including but not limited to, where appropriate, saline or dextrose solutions. The reagent itself must be properly formulated, for example, as a humanized or chimaeric antibody combined with various buffers, sugars, or stabilizing compounds that increase the stability or half life of the antibody. To extend the half-life, the reagent can first be modified to increase or decrease the amount of carbohydrate complexed to it, or alternatively, can be complexed with a reagent such as polyethylene glycol. Finally, pharmaceutical compositions comprising the therapeutic reagent in the appropriate buffers, salts, and pH are required.

Therapeutic kits can comprise the therapeutic compositions of the invention in one or more containers.

6. Monitoring The Effectiveness Of Therapy With Vα12.1-Specific Reagents

The same Vα12.1-specific reagents used to diagnose and/or treat rheumatoid arthritis can also be used to monitor the effectiveness of a disease therapy or to monitor the progression of the disease throughout phases of remission, relapse, or stable periods. Thus, in rheumatoid arthritis, the initial disease correlation is made on the basis of an elevation of Vα12.1 CD8+ T-cells. Vα12.1-specific reagents or other therapeutic reagents can then be used to treat the immune disorder. During the treatment course, as the deleterious T cells are being eliminated, the Vα12.1-specific reagent can be used to monitor the extent of the elimination of the Vα12.1 positive T cells to the point where the cells are gone and the disease is in remission. Following a remission, the Vα12.1-specific reagent is used periodically in rediagnosis, to determine whether the patient is stable, in remission, relapse, or is otherwise in need of treatment. The Vα12.1-specific reagents, especially the monoclonal antibodies of the invention, are thus useful in combined diagnostic and therapeutic procedures.

Deposit Information

Samples of the hybridoma cell line (designated herein as 6D6) that secretes anti-Vα12.1 murine monoclonal antibody were deposited with the American Type Culture Collection, 12301 Parklawn Drive, Rockville, Md., on Aug. 21, 1991 under the terms of the Budapest Treaty and assigned ATCC accession number HB 10858. Without admitting that access to the hybrid cell line is necessary to practice the claimed invention, it is agreed that, upon allowance and issuance of a patent for this invention, all restrictions on the availability of the culture deposit designated herein will be removed and the designated culture will be maintained throughout the effective life of the patent granted, for 30 years from the date of deposit or for five years after the last request for the deposit after issuance of the patent, which ever is longer.

The invention will be more fully understood from the following Examples.

EXAMPLE 1

This example describes the preparation of the anti-Vα12.1 monoclonal antibody designated 6D6.

Establishment of Hybridomas

T cell receptor protein from the HPB-MLT human leukemia cell line was isolated by immunoprecipitation from Triton X-100 (TX-100) lysates of HPB-MLT. For each immunization, 0.5 g of lymphocytes was solubilized in 10 ml of 1% TX-100, was immunoprecipitated with 3 µl of T40/25 ascites, and was adsorbed to 125 µl of 10% (w/v) Staphylococcus aureus Cowan I strain (SACI) (Calbiochem, La Jolla, Calif.). The adsorbed immune complexes were injected i.p. in phosphate-buffered saline (PBS), pH 7.2 into 8-wk-old BALB/c mice at monthly intervals. Mouse sera obtained by tail bleeding were tested by immunoprecipitation on $^{125}$I-labeled HPB-MLT cell lysates to detect the presence of clonotypic or V gene encoded specific mAb and on $^{125}$I-labeled human PBL lysates to detect the presence of mAb against TCR unrelated to HPB-MLT.

Early in the course of immunization, clonotypic monoclonal antibodies and V gene encoded specific monoclonal antibodies could be detected. Immunizations were conducted every two to three weeks for a total period of about six months. To diminish the proportion of mAb directed against the SACI immunoabsorbent, a final i.v. injection of immunoaffinity column-purified HPB-MLT TCR was performed. Briefly, a crude membrane preparation was made from frozen HPB-MLT cells after solubilization in 1% Nonidet P-40. Glycoproteins from this extract were purified by lectin affinity chromatography and passed over a column of mAb T40/25 coupled to Sepharose CL-4B (Pharmacia, Pescataway, N.J.). The bound proteins were eluted from the column with 50 mM diethylamine, pH 11.5 in 0.1% deoxycholate, and the eluted material was neutralized, dialyzed against PBS to remove this detergent, and 0.1% TX-100 was added before injection of 1 µg of the purified HPB-MLT TCR protein. Three days after the i.v. boost, the mouse was sacrificed and spleen cells were removed. Immune spleen cells (2×10$^8$) were fused with myeloma P3X63Ag8.653 cells in the presence of polyethylene glycol 1500 (British Drug House, Carlplace, N.Y.). The fused cells were then selected in the presence of hypoxanthine/aminopterin/thymidine (Sigma, St. Louis, Mo.) in RPMI 1640 (GIBCO, Grand Island, N.Y.) containing 15% fetal calf serum in 24-well tissue culture plates (Flow, McLean, Va.).

Supernatants from wells positive for growth were screened by immunoprecipitation on $^{125}$I-labeled HPB-MLT cell lysates by adding mAb 187.1 (rat anti-mouse$_K$) to insure protein A binding of the mouse hybridoma antibodies. Twenty-three wells produced supernatants that immunoprecipitated the TCR complex from HPB-MLT cells. These were then examined for their ability to immunoprecipitate from and stain HPB-MLT, PBL and other cell lines bearing the same TCR V genes expressed on HPB-MLT cells.

One of the hybridomas that specifically immunoprecipitated HPB-MLT exhibited reactivity with about 2% to 5% of peripheral T cells from normal individuals, as determined by cytofluorographic analysis. See FIG. 1 herein. This monoclonal antibody was given the designation 6D6, and subcloned for further study in accordance with conventional techniques.

Reactivity Of 6D6 mAb

6D6 Reacts Specifically With The T Cell Receptor Of HPB-MLT

Figure 2A:
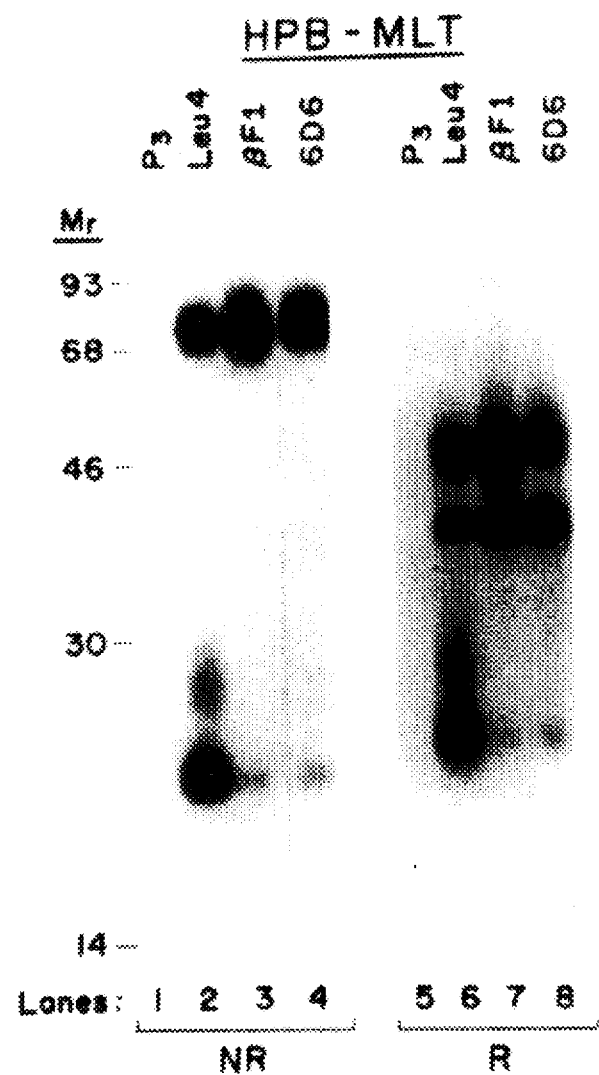
FIG. 2A illustrates that 6D6 immunoprecipitates the T cell receptor α/β heterodimer. Immunoprecipitations of the αβ TCR complex from cell surface $^{125}$I radiolabeled HPB-MLT cells were resolved by SDS-PAGE and analyzed by autoradiography. Antibodies were P3 (negative control), Leu4 (anti-CD3), βF1 (anti-βframework) and 6D6 (anti-Vα12.1). Under non-reducing (NR) conditions (lanes 1-4), the aβ TCR complex was resolved as a 85 kD species by direct immunoprecipitation with mAbs βF1 and 6D6 or by co-immunoprecipitation with anti-CD3 mAb Leu 4. Under reducing (R) conditions (lanes 5-8), the TCR α and β subunits were visualized as 46 kD and 39kD species, respectively. CD3 subunits are present at 20-30kD.

To determine the nature of the molecule recognized by mAb 6D6, immunoprecipitations were performed on $^{125}$I-labeled HPB-MLT cell lysates followed by SDS-PAGE and autoradio-graphy by using Na $^{125}$I and lactoperoxidase as previously described. Brenner, *Nature*, 322:145 (1986). As illustrated in FIG. 2, the mAb immunoprecipitated the TCR αβ heterodimer (85 kd) under non-reducing conditions (FIG. 2A, lane 4). The 85 kd heterodimer resolved into 2 species with Mr 46 kD (TCRα) and 39 kD (TCRβ) under reducing conditions (FIG. 2A, lane 8) For comparison, similar radiolabeled species were visualized after immunoprecipitations with TCR β-specific mAb βF1 and CD3ε-specific mAb Leu 4 (FIG. 2A). In both anti-TCR and anti-CD3 immunoprecipitations, a variable degree of co-immunoprecipitation of the other components was noted. Together, these data indicate that the 6D6 monoclonal antibody is specifically reactive with the T cell receptor of the HPB-MLT clone.

6D6 Is Specific For A Determinant Expressed On The TCR α Chain

To delineate the TCR chain specificity of mAb 6D6, immunoprecipitations were carried out on HPB-MLT cell lysates metabolically labeled with $^{35}$[S] methionine and cysteine.

Biosynthetic labeling of TCR chains from HPB-MLT was carried out as follows. Cells were washed and incubated at $5\times10^6$ cells/ml in methionine- and cysteine-free RPMI-1640 containing 10% dialyzed fetal calf serum (FCS), 2 mM glutamine and 20 mM HEPES at 37° C. in 5% $CO_2$ atmosphere. After 30 minutes, 0.5 mCi each of [$^{35}$S]-methionine and -cysteine were added and incubation continued for 4 hrs. Cells were pelleted and lysed in Tris-buffered saline (TBS, 50 mM Tris pH 7.5, 150 mM NaCl) containing 1% Triton X-100, 1 mM PMSF and 8 mM iodoacetamide. Cell lysates were pre-cleared twice using normal rabbit serum (NRS) and fixed *Staphylococcus aureus* Cowan I (Pansorbin, Calbiochem-Boehring Corp., San Diego, Calif.). Specific immunoprecipitations were carried out using amounts of ascites determined to be optimal; 6D6 (0.1 μl), 3A2 (anti-vβ5.3) (0.4 μl), Leu 4 (anti-CD3) (0.1 μl), βF1 (anti TCR B framework) (0.25 μl) or αF1 (anti-TCR a framework) (0.1 μl). In each case 150 μl of mAb 187.1 (rat anti-mouse K) culture supernatant was added as a second antibody. After 60 min. incubation at 4° C., 100 μl of 10% Protein-A sepharose CL4B (Pharmacia Fine Chemicals, Sweden) was added and incubated further for 30 minutes. Immune complexes were washed in 0.1% Triton X-100, resolved by SDS-PAGE and analyzed by autoradiography as described (Laemmli, *Nature*, 227:680 (1970)).

Figure 2B:
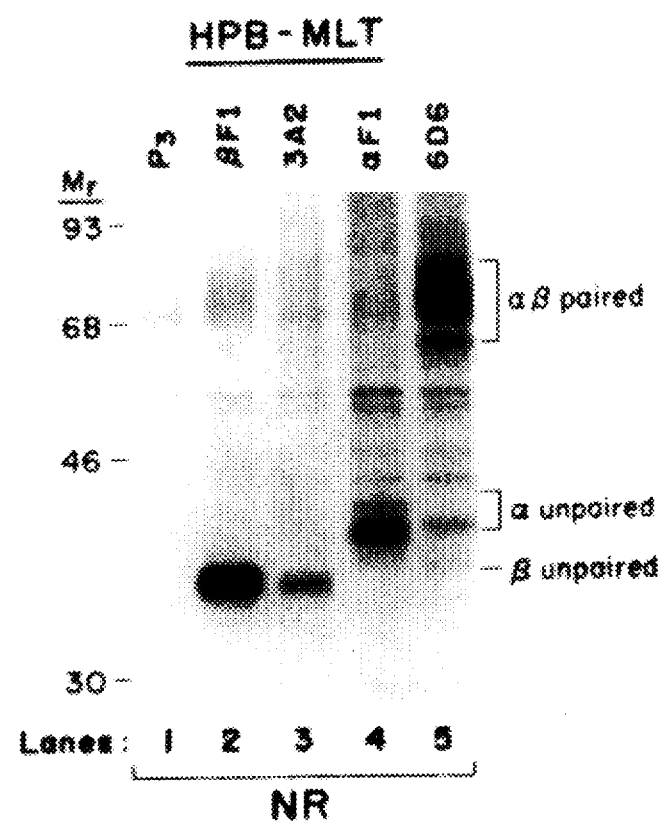
FIG. 2B illustrates that mAb 6D6 recognized a determinant present on the a chain of the HPB-MLT TCR. HPB-MLT cells were metabolically labeled with $^{35}$(S)-methionine and -cysteine for 4 hours and solubilized in 1% Triton X-100. Immunoprecipitations were carried out with the indicated antibodies and resolved by SDS page under non-reducing (NR) conditions and visualized by fluorography. MAbs βF1 (TCR β framework) and 3A2 (anti-Vβ5) immunoprecipitated the unpaired β chain (lanes 2 and 3 respectively). In contrast, αF1 (anti-framework) and 6D6 antibodies (lanes 4 and 5, respectively) immunoprecipitated the unpaired a chain from HPB-MLT lysates. While mAb αF1 immunoprecipitated all of the glycosylated a-chain species identified in HPB-MLT, mAb 6D6 immunoprecipitated the mature form of these species.

Under these conditions, a detectable fraction of the newly synthesized α and β TCR chains were still unpaired, such that mAb 6D6 immunoprecipitated both a free a chain (migrating as a sharp band at 43 kD) and the αβ-heterodimers as fully glycosylated (80–85 kD) and partially glycosylated (70–75 kD) structures (FIG. 2B, lane 5) based on sizes reported earlier (Alarcon et al, *J. Biol. Chem.*, 263:2953 (1988)). Immunoprecipitation with the anti-TCR α framework antibody, αF1, confirmed that the 43 kD species was the unpaired TCR α chain subunit (FIG. 2B, lane 4). The other radiolabeled species (41–44 kD) in the αF1 precipitation presumably corresponded to differentially glycosylated α-chain species, as reported previously. By comparison, other mAbs that were generated including the anti-TCR β framework antibody, βF1 (lane 2), and antibody against the Vβ product of HPB-MLT (3A2) (lane 3) both immunoprecipitated the unpaired β-chain (38 kD) but not any of the free i-chain species. It was thus determined that mAb 6D6 reacted with a determinant expressed on the TCR-α chain.

The Determinant Recognized By 6D6 mAb Is Encoded By The Vα12.1 Gene Segment

To examine whether the determinant recognized by 6D6 was encoded by Vα, Jα, or a combination of both gene segments, 6D6$^+$ clones from healthy individuals were analyzed. Peripheral blood mononuclear cells were separated from heparinized blood from healthy blood donors by Ficoll Hypaque (Pharmacia Fine Chemicals, Uppsala, Sweden) gradient centrifugation, washed twice in RPMI 1640 medium (Gibco, Paisley, UK), macrophage depleted and diluted in phosphate buffered saline. 6D6$^+$ clones were then subcloned as follows.

Peripheral blood mononuclear cells (PBMC) were stimulated in vitro with 100 μg/ml of immobilized mAb 6D6. These cultures were supplemented with conditioned media containing Il-2 after five days of stimulation with the 6D6 mAb. Cells were restimulated with 6D6 mAb (100 μ/ml) and autologous PMBC (4000 rads) two to three weeks after initial stimulation. Within a four or five week period, these cultures contained up to 80% 6D6 positive T cells versus the 3 to 4% in the unstimulated PBL. Cloning and subcloning was achieved by limiting dilutions in media containing IL-2 and a panel of 6D6$^+$ and 6D6$^-$ T-cell clones was derived by staining with 6D6 mAb and other T cell markers. 6D6$^+$ T cells clones included HD5.A and HD5.B.

Genomic DNA was then extracted from the 6D6$^+$ T cell clones HD5.A and HD5.B and a 6D6$^-$ clone, 3A2.D using a standard technique. (Wigler et al, *Cell*, 16:777 (1979)). Briefly, lymphocytes were ficolled to remove dead cells. After PBS wash, cells were transferred to 15 ml Sarstedt tubes and resuspended into 100 μl PBS. Cells were then solubilized in lysis buffer (1×TNE, 0.4% SDS and 100 μg/ml Proteinase K, 2.5 mls for $10^7$ cells) by vigorous pipetting. Tubes were rotated overnight at 37° C. The solubilized cells were then extracted once with 1 volume of chloroform. Two volumes of absolute ethanol were added to precipitate the DNA.

Precipitated DNA was then transferred by plastic pipette to cold (−20° C.) 70% ethanol and washed. After drying the DNA, 900 μl of $H_2O$ and tubes rocked for two hours, after which 100 μl of 10×TE buffer was added. The optical density at 260 was measured to calculate DNA concentration.

The thus-prepared DNA was digested with the restriction enzyme BamHI. 10 μg of DNA was digested overnight in 400 μl of buffer using 50 units of the restriction enzyme. To complete digestion, an additional 50 unit units of enzyme was added and the digestion continued for another three hours. Two volumes of absolute ethanol were added at −20° C. for two hours to precipitate the DNA, making sure salt content was sufficient for precipitation. DNA was then spun and washed once with 70% ethanol and dried in a speed vacuum.

The digested DNA was then resuspended in 36 μl TE buffer, heated for five minutes at 56° C. and 4 μl 10× sample buffer added for loading onto agarose gel for Southern transfers.

5 μg DNA were loaded into a lane of a 0.7% agarose gel and electrophoresed in 1×TBE buffer. Electrophoresis was carried out at 35 volts for 15 hours. The gel was then photographed and denatured for one hour at room temperature in 1.5M NaCl containing 0.5N NaOH. The gel was then reneutralized by washing three times in 1.5M NACl with 1M Tris, pH 8. DNA was then transferred from the agarose gel to Hybond-N nylon membrane (AMERSHAM) overnight in 20×SSC. The membrane was then rinsed in 6×SSC and DNA was crosslinked to the membrane by UV irradiation (4 min).

Vα12.1 DNA was radiolabeled by hexapriming using 100 μg of DNA insert, (pGA5, Sim et al, previously cited). The Vα12.1 probe was an ECO-RI-ACC I fragment of the TCR α chain cDNA clone pGA5. Hybridization was carried out using standard conditions. Briefly, approximately $10^6$ cpm/lane was incubated in sealed plastic bags containing 50% formamide, 6% SSC, 5×Denhardt's reagent, 0.5% SDS, 50 Mm Hepes, and 200 μg of ssDNA (salmon sperm) overnight at 42° C. Blots were washed once in 1×SSC containing 0.5% SDS at 42° C. (or 50° C.). Autoradiography was carried out by exposing the blots to x-ray film at −70° C.

Figure 3:
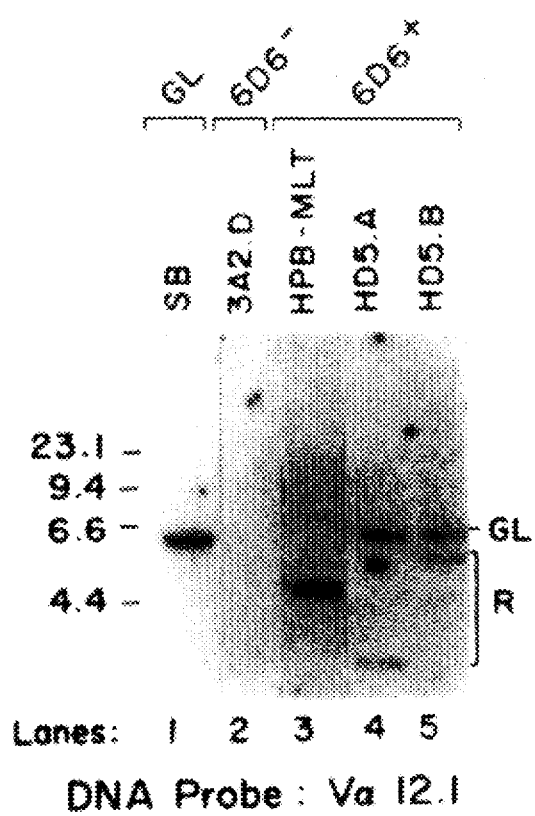
FIG. 3 illustrates that the Vα12.1 gene segment is rearranged in all cells recognized by mAb 6D6. DNA from 6D6$^+$ T-cell clones HD5.A (lane 4) and HD5.B (lane 5), T-cell leukemia cell line HPB-MLT (lane 3), and the 6D6$^-$ T-cell clone 3A2.D were digested with Bam HI and analyzed by Southern hybridization using a Vα12.1-specific probe. Germline configuration (GL) for Vα12.1 gene was seen as a 6.3 Kb fragment in the B cell line, SB (lane 1). While both Vα2.1 alleles in 3A2.D T-cell clone were deleted, DNA from HD5.A, HD5.B and HPB-MLT showed distinct Vα12.1 rearrangements (R).

As shown in FIG. 3, the germ line configuration (GL) for the Vα12.1 gene was seen as a 6.3 kb fragment in the B cell, SD (lane 1). Both Vα12.1 alleles in 3A2 D T cell clone were deleted, while DNA from the 6D6$^+$ clones HD5.A and HD5.B and that from the HBP-MLT line showed distinct rearrangements.

The fact that the rearranged fragments were of different sizes in each cell line indicated that the Vα12.1 gene segment, which is part of a V family having only one member, might be rearranging to several different Jα segments. This suggested that mAb 6D6 was recognizing a Vα rather than a Jα gene segment encoded determinant.

In order to understand the relationship between Vα12.1 gene usage and the expression of the determinant recognized by 6D6, alpha chain junctional sequences from three 6D6$^+$ T cell clones (HD5.A and HD5.B and HPB-MLT) were sequenced.

To clone and sequence the junctional sequences of the 6D6+ T cell clone alpha chains, Vα12.1 and Cα specific oligonucleotide primers were used in polymerase chain reaction (PcR). These products were cloned into M13 phage DNA by using cloning sites synthetically introduced into the PCR primers.

The ligated M13 phage DNA was cloned by plating into JM101 bacterial cell. Phage plaques containing PCR products were isolated and LB broth containing 1/100 dilutions of JM101 cells were inoculated. Phage were grown for 4.5 hours at 37 C. 1.5 mls were then poured into and spun in microfuge tubes and spun for five minutes at room temperature. 1.2–1.3 ml of supernatants containing 150–200 μl 20% polyethylene glycol (PEG) containing 2M NACl and magnesium sulfate (MS) were pipetted and cells mixed and incubated at room temperature for 15 minutes. The phage pellets were spun down and the supernatant discarded. Pellets were then resuspended in 100 μl of 10 mN Tris pH 8.0 with 0.1 mM EDTA and extracted with 100 μl of phenol equilibrated with 10 mM Tris 8.0, 0.1 mM EDTA. Supernatant was added to a tube containing 300 μl of ethanol with 3M sodium acetate. Incubation was conducted for two hours at 20° C., followed by spinning for 15 minutes at 4° C. The DNA pellets were then washed and dried in a speed vacuum and resuspended with 30 μl of 10 mM Tris 8.0 and 0.1 mM EDTA. Phage yield was 5–10 μg per mini prep.

Sequencing was conducted by the dideoxy chain termination method using modified T7 polymerase (Sequenase, United States Biochemical Corp, Cleveland, Ohio). 5 μl of phage DNA containing inserts were used in the sequencing by annealing a universal primer to the M13 sequences close to the insertion site and the appropriate amount of deoxynucleotides provided in combination with one of four deoxynucleotide triphosphate analogs that terminate DNA extension. Each of the four separate reactions were analyzed in separate lanes on sequencing gels. The patterns of dideoxynucleotide incorporation were visualized by autoradiography due to the incorporated deoxynucleotide. Sequences were analyzed and Vα12.1 and Cα specific sequences were lined up with published sequences.

The results of the sequencing analysis revealed that each of the three 6D6$^+$ T cell lines contained in frame Vα12.1 rearrangements to distinct Jα gene segments. These results demonstrate that the mAb 6D6 specifically recognized the product encoded by the Vα12.1 gene segment.

EXAMPLE 2

This example determines the percentage of expression of the Vα12.1 gene segment in peripheral blood T-cell subsets in normal, healthy individuals.

Peripheral blood samples were obtained from 20 healthy adult blood donors. Peripheral blood mononuclear cells (PBMC) were then separated from heparinized peripheral blood by Ficoll-Hypaque (Pharmacia Fine Chemicals, Uppsala, Sweden) gradient centrifugation. Heparinized blood was also obtained from the umbilical cords of 10 newborn humans of uncomplicated deliveries at the Brigham and Women's Hospital.

The PBMC and CBMC from each of the subjects were analyzed by a two color staining procedure, to determine the percentage of 6D6$^+$ T cells in CD4$^+$ and CD8$^+$ T subsets.

All cells were washed in tissue culture media (RPMI-1640) containing 10% fetal calf serum (FCS). Isolated PMBC or CBMC were suspended in phosphate buffered saline containing 2% pooled human serum and 0.2% sodium azide (staining buffer) Fifty μl of cell suspension containing $10^5$ PMBC or CBMC were incubated with directly conjugated antibodies by adding an equal volume of antibody premix containing 5 μg/ml of biotinylated 6D6 (red fluorescence) with 5 μg/ml of fluorescein isothiocyante (FITC)-OKT4 (anti-CD4, Ortho Pharmaceuticals, Raritan, N.J.) or FITC-OKT8 (anti-CD8, Ortho) monoclonal antibodies (green fluorescence). After one hour of incubation on ice, cells were washed twice and resuspended in 50 μl of Streptavidin-Phycoerytherine (PE) and incubated for 30 minutes to allow biotin-avidin binding. After 30 minutes the cells were washed thrice and resuspended in 400 μl of staining buffer containing 1.25 ng/ml of propidium iodide (PI). Two color FACS analysis was then carried out with a FACSCAN (Becton Dickinson, Mountain View, Calif.).

Lymphocytes were gated on the basis of forward and side scatter and dead cells were gated out by staining with propidium iodide and $10^4$ cells were analyzed for fluorescence. Optimal compensation was set for green and orange fluorescence.

Figure 4A:
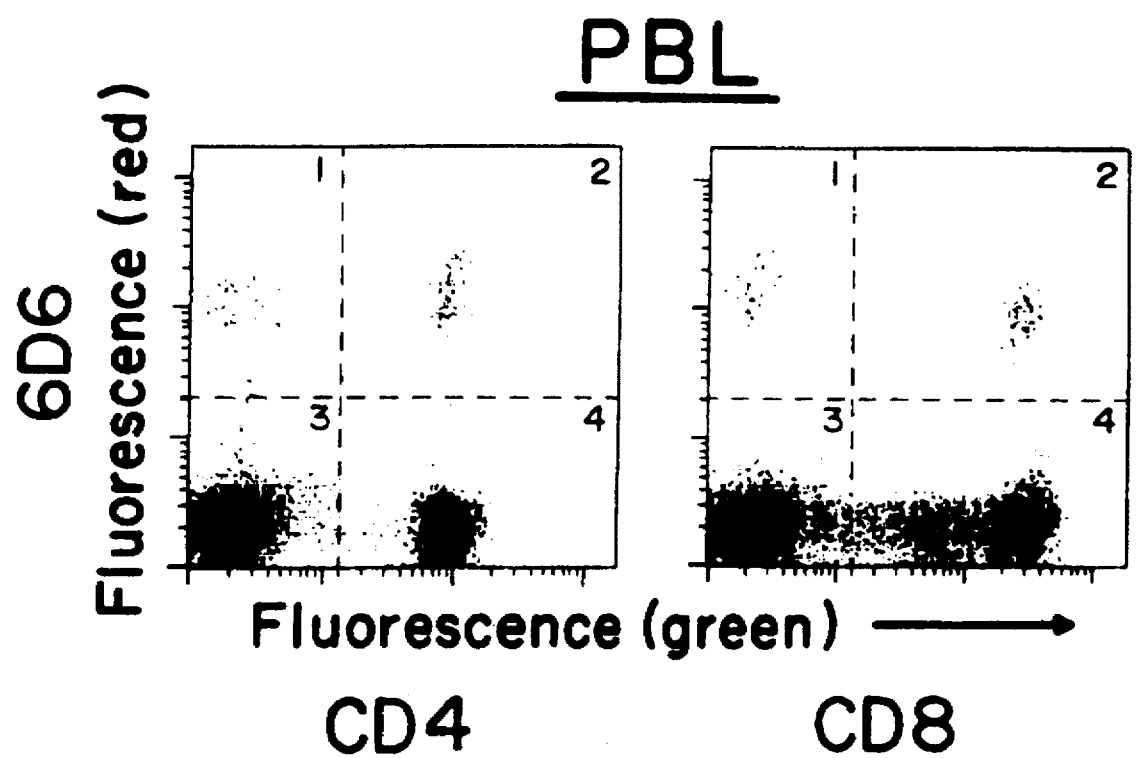
FIG. 4A illustrates the Vα12.1 expression in CD4$^+$ and CD8$^+$ T cells from adult and newborn peripheral blood lymphocytes, as determined by FACS two color immunofluorescence analysis. PBMC from a normal healthy adult and a newborn were stained with anti-CD4 (OKT4) or anti-CD8 (OKT8) (green fluorescence, FITC) and anti-Vα12.1 (6D6) (red fluorescence, PE) mAbs as described in Example 2. Lymphocytes were gated on the basis of forward and side scatter profiles (not shown) and analyzed for fluorescence intensity in log scale. Dot plots were divided into quadrants to represent unstained cells (lower left, quadrant 3), cells stained with FITC alone (lower right, quadrant 4), cells stained with PE alone (upper left, quadrant 1) and cells that double stained with FITC and PE (upper right, quadrant 2).

The results of an analysis of a peripheral blood sample from a normal, healthy blood donor for Vα12.1 expression among CD4$^+$ and CD8$^+$ T cells by two color staining is shown in FIG. 4A. In this Figure, PBMC from an adult were stained with FITC-OKT4 and FITC-OKT8 (green fluorescence) and anti-Vα12.1 (6D6) (red fluorescence) and analyzed as described above.

Dot plots were divided into quadrants to represent unstained cells (lower left, quadrant 3), cells stained with FITC alone (lower right, quadrant 4), cells stained with PE alone (upper left, quadrant 1) and cells that double stained with FITC and PE (upper right, quadrant 2).

The Vα12.1 expression in CD4$^+$ and CD8$^+$ T lymphocytes from adult and newborn cells (see FIG. 4B) was determined using data for individual blood samples stained as in FIG. 4A. The expression of Vα12.1 in the CD4$^+$ and CD8$^+$ subsets for each individual are connected by a line. The following formula was used in the calculation of percentage values for 6D6 reactivity with CD4$^+$ or CD8$^+$ T cells.

$$\% \text{ 6D6}^+ \text{ cells} = \frac{\text{6D6}^+ \text{ cells co-stained with CD4 (or CD8) in PBMC (2nd quadrant)}}{\text{CD4}^+ \text{ (or CD8}^+\text{) cells of total T-cells (2nd + 4th quadrant)}} \times 100$$

Figure 4B:
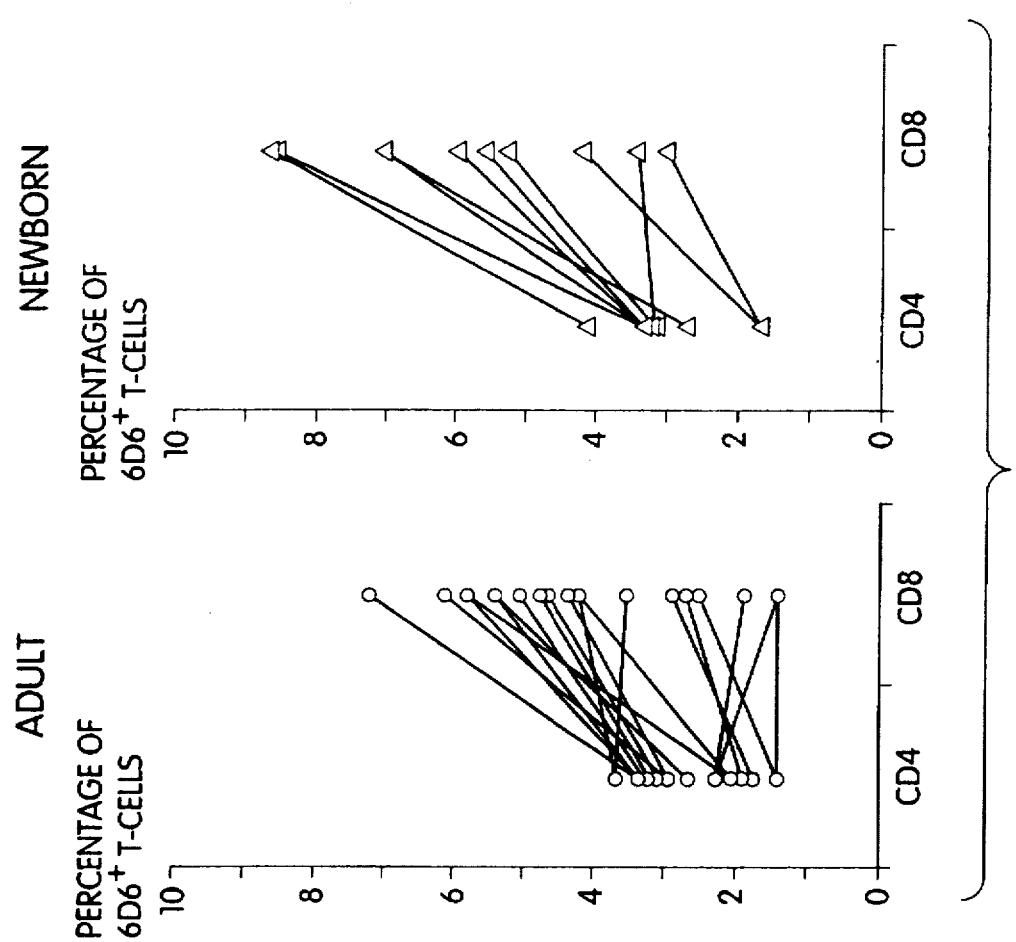
FIG. 4B illustrates the Vα12.1 expression in CD4$^+$ and CD8$^+$ T cells from 20 normal healthy adults and 10 newborns The expression of Vα12.1 in CD4$^+$ or CD8$^+$ T subsets for each individual are connected by a line. The formula used to calculate the percentage value for 6D6 expression in $CD4^+$ or $CD8^+$ T cells is set forth in Example 2.

As illustrated in FIG. 4A and 4B, when Vα12.1 gene expression was analyzed among the CD4$^+$ and CD8$^+$ T cells by two color staining, Vα12.1 was expressed on about 1.4 to about 3.75% (mean 2.66%±0.68%) of CD4$^+$ T cells of normal healthy adult blood donors, while Vα12.1 was expressed on about 1.4 to about 7.2% (mean 4.2±1.62%) on the CD8$^+$ T cells of the same individuals. Most individuals therefore expressed a 2–3 fold higher frequency of Vα12.1 among CD8$^+$ compared to CD4$^+$ T cells. This was also true in newborns. See FIG. 4B. Vα12.1 was expressed on about 1.7 to about 4.1% (mean 12.94%±0.74%) of CD4$^+$ T cells of normal newborns, while Vα12.1 was expressed on about 3.0 to about 8.8% (mean 5.92±12.03%) on the CD8$^+$ T cells of the same newborns.

EXAMPLE 3

This example demonstrates an expansion of Vα12.1 gene usage in a subset of rheumatoid arthritis patients.

Expression of Vα12.1 gene usage in a total of 80 patients with several autoimmune diseases, including rheumatoid arthritis (46 patients), osteoarthritis, polymyosistis, and systemic lupus erythematosus, was examined using the Vα12.1 mAb as in Example 2, except that peripheral blood samples were obtained from patients showing clinical symptoms of the respective diseases. Briefly, flow cytometric analyses were performed using directly conjugated antibodies. Heparinized blood was obtained from individuals and PBMC were isolated using Ficoll-Paque (Pharmacia Fine Chemicals, Uppsala, Sweden) and suspended in staining buffer (PBS/2% human serum with 0.02% NaN$_3$) containing saturating amounts of conjugated mAbs and analyzed by a Facscan Flow cytometer (Becton Dickinson). Two-color immunofluorescence analysis of Vα12 expression on CD4$^+$ and CD8$^+$ T cells was carried out on peripheral blood mononuclear cells (PBMC) using OKT4 (anti-CD4) or OKT8 (anti-CD8) FITC conjugated mAb and anti-Vα12 mAb (6D6-PE) as previously described using a FACSCAN (Becton Dickinson and Co., Mountainview, Calif.). Lymphocytes were gated on the basis of forward and side scatter profiles and analyzed for fluorescence intensity in log scale. Ten thousand viable cells were analyzed by gating on lymphocytes excluding propidium iodide. The data were analyzed by dividing the dot plot into quadrants to represent unstained cells, cells stained with FITC alone (OKT4 or OKT8), cells stained with PE alone (6D6), and cells that were co-stained with FITC and PE. The Vα12 expression on CD4$^+$ and CD8$^+$ T cells from adult RA patients was determined using data generated for individual peripheral blood samples stained as in Example 2. The following formula was used to calculate the percentage value for Vα12 expression: % Vα12$^+$/CD4$^+$ (or CD8$^+$) cells={Vα12$^+$ cells co-stained with anti-CD4 (or anti-CD8) (2nd quadrant)/% T cells that were CD4$^+$ (or CD8$^+$)}×100. The results are summarized in FIG. 5.

Figure 5:
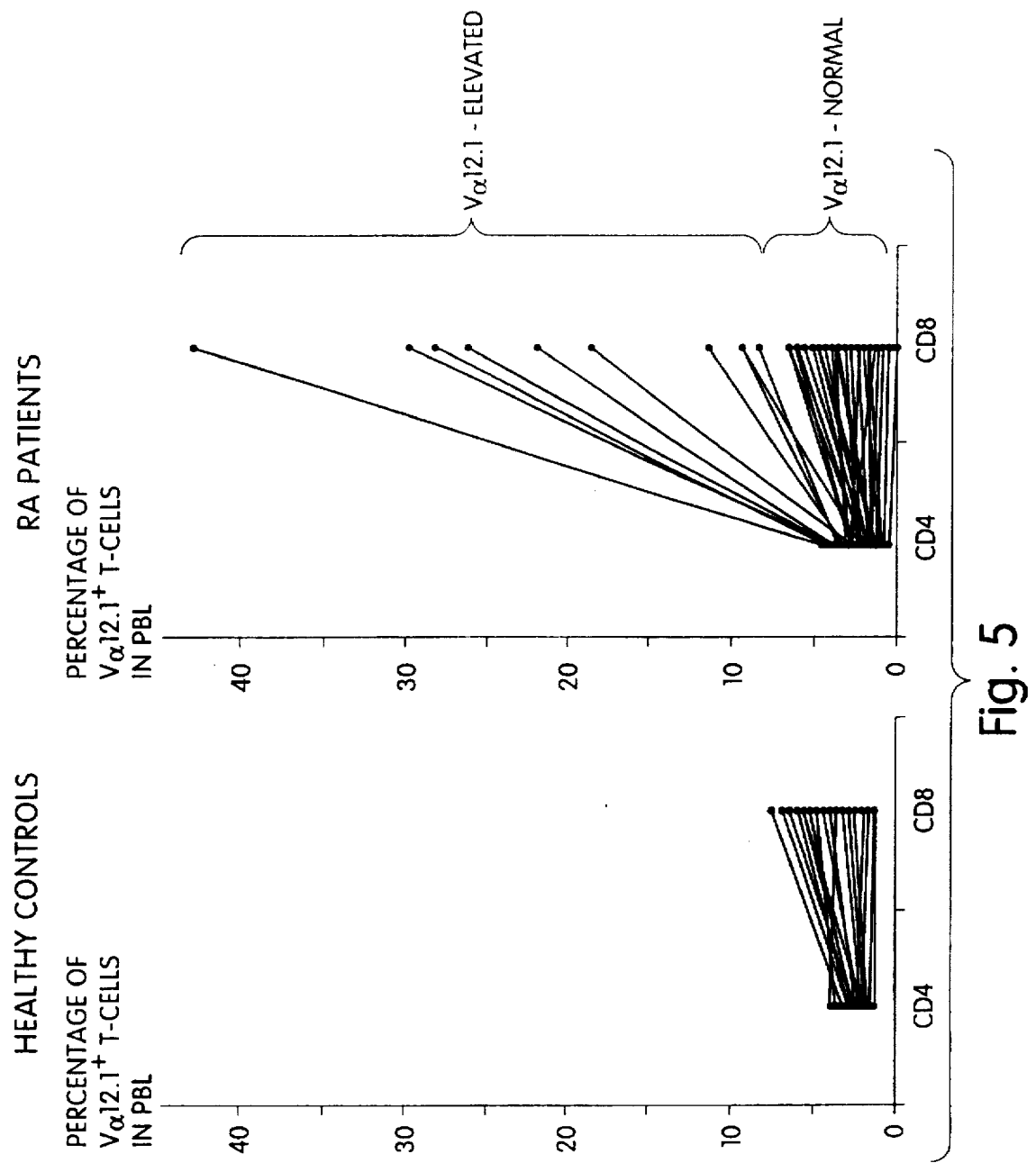
FIG. 5 illustrates the elevated expression of $V\alpha 12.1$ $CD8^+$ T cells in a subset of rheumatoid arthritis patients when compared to T cells from healthy individuals. The percentage of $mAb\ 6D6^+$ ($V\alpha 12.1$ bearing) in CD4 and CD8 T cell subsets was determined as in FIG. 4.

As illustrated in FIG. 5, one group of patients contained percentages of Vα12.1 bearing CD8$^+$ T cells (mean value of 3.6%, range 1.0% to 7.0%) which was similar to those found in normal subjects. However, the distribution was bimodal, as a second group of patients had much higher percentages of Vα12.1$^+$ T cells (mean value of 22%, range 8.0% to 43%) in the CD8$^+$ T subset. This Vα12-elevated group of patients had greater than the 2×SD (7.3%) of the mean in healthy individuals tested (3.6%). Each of the eight patients in this group, sometimes hereinafter referred to as the Vα12-elevated group, contained 43%, 29%, 22%, 27%, 26%, 20%, 12, and 9% Vα12.1 bearing CD8$^+$ T cells, respectively. The high percentages of Vα12.1$^+$ cells in these patients was a relatively stable phenomenon as patients tested over approximately a one year period showed consistent levels. The increased numbers of Vα12.1 cells were not noted in the CD4$^+$ subpopulation of T cells.

EXAMPLE 4

To gain insight into the basis for the Vα12.1 T cell expansion in RA, Vα12.1 transcripts from selected CD8$^+$ T cells from three patients exhibiting the expansion were cloned and sequenced. Nucleic acid sequences of Vα12.1-containing transcripts were generated by direct (Vα12.1-specific) or inverse polymerase chain reaction (PCR) (all Vα's). Isolation of CD8+, Vα12.1+ Cells CD8$^+$, Vα12.1$^+$ T lymphocytes from two RA patients exhibiting an expansion of Vα12.1 were obtained from the patient's peripheral blood and isolated using a two-step selection procedure. Separation of the CD4$^+$ and CD8$^+$T cells was carried out by Ficoll-Paque (Pharmacia Fine Chemicals, Uppsala, Sweden) on the isolated cells, which were suspended in RPMI-1640 containing 5% fetal calf serum (FCS) at 5×10$^5$ /ml for mixing with saturating amounts of anti-CD4 (OKT4) monoclonal antibodies (mAb). The first selection was carried out by rotating the cell suspensions for 1 hour at 4° C. and washing away free antibody with RPMI/5% FCS before adding a 1 to 2 fold excess of goat anti-mouse Ig conjugated Dynabeads (Dynabeads M-450, Dynal, Oslo, Norway). Cells bound to the beads (CD4$^+$) were removed. CD4-depleted populations of cells were reselected twice more with beads to remove completely any residual CD4$^+$ T cells. Under these conditions, the CD8$^+$ T cells were enriched to greater than 98% purity, as verified routinely by staining the negatively selected populations by FACS. A second step of selection with anti-Vα12.1 (mAb 6D6) was carried out on the CD8-enriched cells in order to isolate Vα12.1$^+$/CD8$^+$ T cells. Double selected cells (Vα,12.1$^+$, CD8$^+$) are washed extensively before solubilizing in RNA lyses buffer for RNA isolation for use in the polymerase chain reactions.

RNA Purification

Purification of RNA from CD8$^+$ or Vα12.1$^+$/CD8$^+$T cells was carried out according to Chomczynski and Sacchi, *Anal. Biochem.*, 162:156 (1987). Total RNA was quantitated and analyzed for intactness by resolution on a 1% agarose mini-gel and visualization upon staining with ethedium bromide.

Direct Polymerase Chain Reaction

Complementary DNA (cDNA) for the direct PCR method was synthesized at 42° C. in 50 μl reactions using 500 ng of oligo-(dt)$_{12-18}$ primer, 1 to 5 μg total RNA and 10 U AMV reverse Transcriptase (Promega Corp., Madison, Wis.). After 1 hour, the reaction mixture was diluted to 100 μl, boiled, chilled, and centrifuged to remove insoluble material. PCR was performed in 25 μl reactions containing 1 μl cDNA (1/100), 1 MM MgCl$_2$, 10 mM Tris pH 8.3, 1 mg.ml gelatin, 5 picomole of each primer, 0.2 mM of each dNTP and 2 U of Taq Polymerase (Thermus aquaticus DNA polymers, Perkin-Elmer-Cetus Corp.).

Briefly, cDNA and primers were pre-mixed with MgCl$_2$/Tris/gelatin buffer and heated at 95° C. for 7 min. Other components were added, the reaction mixture was overlain with mineral oil, and 25 to 35 cycles of PCR were carried out in a thermocycler (Perkin-Elmer-Cetus Corp.) at the following settings: 0.7 min. at 95° C. for denaturation, 1 min. at 56° C. for annealing, and 1 min. at 72° C. for chain extension. To ensure complete synthesis, the last cycle at 72° C. was extended to 10 min. The Vα12.1 and Cα primers used were the same as those used and illustrated in DerSimonian et al., *J. Exp. Med.*, 174:639, 640 (September, 1991). See, also Sim et al., *Nature*, 312:771–75 (December 19984) for the complete nucleic acid sequence of the TCR α chain from HPB MLT. The Sal I and HindIII restriction sites in the respective PCR primers were used to generate sticky ends for cloning.

Inverse Polymerase Chain Reaction

Inverse PCR (iPCR) was first established to amplify the flanking region of a known sequence within a given restriction fragment of genomic DNA. Recently, this method was shown to be applicable to the amplification of the full length cDNA of TCR α and β genes. Uematsu, *Immuno-genetics*, 34:174 (1991); Uematsu et al., *Proc. Natl. Acad. Sci. U.S.A.*, 88:8534 (1991).

To identify all of the Vα and Jα gene segments present in the Vα12.1$^+$/CD8$^+$ T cells, we used the iPCR method, which does not require prior sequence information on both ends of the DNA to be amplified. This technique independently confirmed our findings generated by the direct PCR method.

First strand cDNA for iPCR was synthesized using RNA from CD8$^+$, Vα12.1$^+$T lymphocytes by priming with an oligo-(dT)$_{12-18mer}$ and utilizing moloney murine leukemia virus-derived reverse transcriptase (MMLV-RT) lacking RNase H activity (Gibco BRL). For oligo-dT priming, 1 μg total RNA (1 μg/μl) was mixed with 0. 5 μl oligo-(dT) (100 ng/μl) in 10. 5 μl water, incubated at 65° C. for 10 minutes, rapidly chilled at 4° C. and then spun down. For first strand synthesis, 4 μl of 5X reaction buffer, 2 μl of 0. 1M DDT and 1 μl of 10 mM dNTP were added to the primed RNA mixture, the thus-prepared mixture was then vortexed gently and preincubated at 45° C. for 2 minutes. 1 μl (200 units) of MMLV-RT (RNase H$^-$) was added and the mixture incubated at 45° C. for 60 minutes.

For second strand cDNA synthesis, RNase H was used to nick the mRNA strand of the RNA/DNA hybrid, generating a series of RNA primers that served to synthesize the second strand DNA with *E. coli* DNA polymerase I and *E. coli* DNA ligase. The double-stranded cDNA thus prepared was blunt ended using the 3'–5'exonuclease activity of T4 DNA polymerase of DNA was circularized using T4 DNA ligase. This circular cDNA was used as the template for the iPCR amplification by using a pair of Cα primers, which were oriented in an outward direction from one another.

Briefly, 1 μl of the circularized DNA was admixed with 34.5 μl water, 5 μl 10×PCR buffer; 5 μl of 20 mM MgCl$_2$; 1 μl of dNTP (10 mM each) 1.5 μl of each primer (10 pM/μl) and 0.5 μl Taq polymerase (5 u/μl) for a total of 50 μl and the mixture was overlain with mineral oil. Thirty five cycles of PCR were carried out in a thermocycler (Perkin-Elmer-Cetus Corp.) at the following settings: 0.5 min. at 95° C. for denaturation, 0.5 min. at 62° C. for annealing, and 1 min. at 72° C. for chain extension. To ensure complete synthesis, the last cycle at 72° C. was extended to 10 min.

After PCR, 5 μl of 100 mM MgCl$_2$ and 0.5 μl of E. coli DNA polymerase I (Klenow fragment) were added to the mixture and incubated for 30 min. at 37° C. PCR products were then checked on a minigel in accordance with established protocols.

This method generated PCR products of approximately 700 base pairs length for the TCRα transcripts. This method generated up to 2×10$^6$ primer specific cDNA clones starting with as little as 1 μg of total RNA (Uematsu 1991). In our experience, we were able to generate a library of TCR α cDNA products from RNA isolated from as little as 2×10$^4$ of fresh peripheral T cells. The Cα forward primer contained an artificial Sal I site and the Cα inverse primer contained a Not I site, which facilitated DNA cloning and sequencing.

The buffers used in the inverse PCR reaction are as follows:

5×2nd-strand buffer 94 mM Tris-HCl, pH 6.9, 453 mM KCl, 23 mM MgCl$_2$, 750 μMβ-Nicotinamide dinucleotide, 50 mM ammonium sulfate;

5×circularization buffer 250 mM Tris-HCl, pH 7.6, 50 mM MgCl$_2$, 25% w/v polyethylene glycol (PEG) 8000, 5 mM ATP, 5 mM DTT;

10×PCR buffer 670 mM Tris-HCl, pH8.8, 166 mM (NH$_4$)$_2$SO$_4$, 1 mg/ml BSA.

Cloning and Sequencing of PCR Products

Appropriately sized DNA products were isolated from low melting point (LMP) agarose gels (BRL, Gaithersburg, Md.) and ligated to the M13 vector with cloning sites. Cloning and sequencing were carried out by the dideoxy chain termination method using the modified T7 polymerase (Sequenase; United States Biochemical Corp., Cleveland, Ohio) Sanger et al., *Proc. Natl. Acad. Sci. USA*, 74:5463 (1977). The sequencing products were resolved on polyacrylamide gels and autoradiography was carried out according to standard methods.

Clonality of the Vα12.1 Expansion

The cDNA sequences of the Vα2.1 containing-transcripts are set forth in Table 1 below and also in the Sequence Listing. Sequences comprise the most 3' nucleotides (11 to 14) of the variable region Vα12.1 and complete Jα gene segments. All sequences are presented in the 5' to 3' direction. The 3' Vα12.1 and Jα-containing sequences are separated for in Table 1 for the sake of illustration.

TABLE 1

| DIRECT PCR: | |
|---|---|
| Patient 1 - | |
| 3' Vα12.1: | TGTGCTCTGAGTGA- |
| Jα Sequence: | -CGGCTATGGTCAGAATTTTGTCTTTGGTCCC GGAACCAGATTGTCCGTGCTGCCCTAT |
| # of Clones: | 15/15 |
| Vα/Jα Usage: | Vα12.1/JαA1 |
| Patient 2 - | |
| 3' Vα12.1: | TGTGCTCTGAGTGA- |
| Jα Sequence: | -TTATCAGGGCGGATCTGAAAAGCTGGTCTTT GGAAAGGGAATGAAACTGACAGTAAACCCATAT |
| # of Clones: | 9/16 |

TABLE 1-continued

| | |
|---|---|
| Vα/Jα Usage: | Vα12.1/JαA12 |
| Patient 3 - | |
| 3' Vα12.1: | TGTGCTCTGAG- |
| Jα Sequence: | -AGGGGGAGGTGCTGACGGACTCACCTTTGGC AAAGGGACTCATCTAATCATCCAGCCCTAT |
| # of Clones: | 16/24 |
| Vα/Jα Usage: | Vα12.1/JαA6 |
| 3' Vα12.1: | TGTGCTCTGAGTGA- |
| Jα Sequence: | -GCCTTATTCAGGAGGAGGTGCTGACGGACTC ACCTTTGGCAAAGGGACTCATCTAATCATCC AGCCCTAT |
| # of Clones: | 3/24 |
| Vα/Jα Usage: | Vα12.1/JαA6 |
| INVERSE PCR | |
| Patient 1 - | |
| 3' Vα12.1: | TGTGCTCTGAGTGA- |
| Jα Sequence: | -CGGCTATGGTCAGAATTTTGTCTTTGGTCC CGGAACCAGATTGTCCGTGCTGCCCTAT |
| # of Clones: | 9/9 |
| Vα/Jα Usage: | Vα12.1/JαA1 |
| Patient 3 - | |
| 3' Vα12.1: | TGTGCTCTGAG- |
| Jα Sequence: | -AGGGGGAGGTGCTGACGGACTCACCTTTGG CAAAGGGACTCATCTAATCATCCAGCCCTAT |
| # of Clones: | 21/27 |
| Vα/Jα Usage: | Vα12.1/JαA6 |
| 3' Vα12.1: | TGTGCTCTGAGTGA- |
| Jα Sequence: | -GCCTTATTCAGGAGGAGGTGCTGACGGACT CACCTTTGGCAAAGGGACTCATCTAATCAT CCAGCCCTAT |
| # of Clones: | 5/27 |
| Vα/Jα Usage: | Vα12.1/JαA6 |

As illustrated in Table 1 of this Example, in each of the three patients analyzed, we identified repeated Vα12.1-containing clones corresponding to distinct functional TCR α chain transcripts. For example, in patient #1 where 43% of the $CD8^+$ T cells were $Vα12.1^+$, all 15 DNA clones analyzed by direct PCR had identical sequences. Similarly, 9 of 16 (56%) Vα12.1containing DNA clones were identical in patient #2, where 26% of the PBL $CD8^+$ T cells were $Vα12.1^+$. In patient #3 where 28% of the peripheral $CD8^+$ T cells were $Vα12.1^+$, we identified 2 repeated sequences, one was represented in 16 of 22 DNA clones (73%), and a second repeated sequence was identified in 4 of 22 DNA clones (18%). The remaining two clones were identified only once. Although the junctional sequences were different, both of these Vα12.1 encoded sequences in this patient used the JαA6 gene segment. Furthermore, the independent use of inverse PCR (iPCR) to clone and sequence Vα-containing transcripts in CD4 depleted and positively selected for Vα12.1 bearing T cell populations was also assessed. This permitted the amplification of all TCR Vα transcripts present in $Vα12.1^+/CD8^+$ selected T cells. By this method, 9 of 9 DNA clones (100%) from patient #1 were identical, but distinct from a repeated sequence found in 21 of 27 DNA clones (78%) from patient #3. These sequences match exactly the repeated sequence generated by the direct PCR method, respectively. Moreover, the second clonal population of Vα12.1 to JαA6 recombination as seen in patient #3 (by the direct method) was also independently confirmed by the iPCR method, where 5 of 27 DNA clones (19%) were found to be identical. Thus, two independent methods of generating TCR Vα specific PCR products validate each approach and confirm the oligoclonality of Vα12.1 expansion in RA.

Notably, all of the repeated $Vα12.1^+$ T cell rearrangements in the 3 patients analyzed use either JαA1 (patient #1), JαA12 (patient #2) or JαA6 (patient #3) each of which encodes a common sequence at the 3' end of Jα gene segment. This short stretch of shared residues (pro-tyr) is predicted to contribute (or is immediately adjacent) to the third complementarily determining region (CDr3) and thus may play a role in antigen or MHC recognition. Interestingly, only six of the 80 known Jα gene segments encode this two amino acid sequence stretch. The striking occurrence of repeated sequences found in these patients was not observed in similar analysis of normal subjects, and it suggests a corresponding clonality of $Vα12.1^+$ T cells in the patient's peripheral blood.

EXAMPLE 5

This Example examines the surface expression of several activation markers on the peripheral Vα12.1 T cells in RA patients and demonstrates that the expanded $Vα12^+$ T cells in RA were previously activated.

The cell surface expression of DR, IL-2R α and β chains, CD45RO, VLA-1, and transferrin receptor on CD8+, Vα12.1+ cells from three RA patients were analyzed as described in Example 3. Ma\Abs LB3.1 (anti-HLA DR), B1.49.9 (anti-IL-2Rα), Tu27 (anti-IL-2Rα), UCHL1 (anti-CD45RO), TS2/7 (anti-VLA-1), 5E9 (anti-transferrin receptor) conjugated with PE were used to assess the activation and memory surface antigen phenotype of the $Vα12.1^+$-elevated $CD8^+$ T cells in RA. The percentage expression of each of the receptors from the cells of the three patients was calculated using the following formula: $Vα12.1^+$ T cells: % LB3.1 (or other activation antigens) /$Vα12^+$ (or $CD8^+$) cells ={$LB3.1^+$ cells co-stained with anti-Vα12.1 (or anti-CD8) (2nd quadrant)/% T cells that were $Vα12^+$ (or $CD8^+$)}×100.

The results revealed that, similar to most $CD8^+$ T cells, Vα12.1 T cells in RA patients expressed only IL-2R β chains. No significant amount of freshly isolated T lymphocytes expressed the high affinity IL-2R αβ chains. Further, the transferrin receptor was not expressed on the Vα12.1 elevated population of cells. However, CD45RO was expressed on the majority of the Vα12.1 cells indicating a memory phenotype. These results argue that the majority of Vα12.1 cells in circulation in these RA patients were not acutely activated, but had previously been activated. In addition, 10 to 30% of $Vα12.1^+$ T cells expressed VLA-1 and HLA-DR, suggesting ongoing activation for a minor subpopulation of these cells.

EXAMPLE 6

This Example reveals that the expansion of Vα12.1 in $CD8^+$ T cells of a subset of RA patients correlates with an increase in the occurrence of the HLA-DQW2 allele.

The MHC alleles present in eight patients from the Vα12.1-elevated group were compared to those with Vα12.1-normal group of RA patients. Serologic HLA typing for the RA patients was carried out at the Brigham & Women's HLA laboratory (Boston, Mass.) in accordance with established techniques. The results of the HLA-typing for the 8 Vα12.1-elevated patients are illustrated in Table 2 of this Example.

TABLE 2

HLA Tissue Typing

| RA PATIENTS: | CLASS I | | CLASS II |
|---|---|---|---|
| Patient #1 | A_, B44, | :DR7, | DQw2 |
| (6D6+/CD8+:43%)* | A32, B60, Cw3 | :DR4, | |
| Patient #2 | A1, B8 | :DR3, | DQw2 |
| (6D6+/CD8+:29%) | A2, B_, | :DR4 | |
| Patient #3 | A2, Bw52 | :DR3, | DQw2 |
| (6D6+/CD8+:22%) | A11, B48 | :DR10, | |
| Patient #4 | A2, B35, Cw4 | :DR1, | DQw1 |
| (6D6+/CD8+:27%) | A11, Bw57, Cw3 | :DR2, | |
| Patient #5 | A30, B14 | :DR7, | DQw2 |
| (6D6+/CD8+:26%) | A23, B13 | :DR1, | DQw1 |
| Patient #6 | A23, B27, Cw2 | :DR4, | DQw2** |
| (6D6+/CD8+:20%) | A24, Bw42, | :DR5, | |
| Patient #7 | A2, B7, | :DR3, | DQw2 |
| (6D6+/CD8+:12%) | A29, B44, | :DR7, | DQw4 |
| Patient #8 | A30, B7, | :DR3, | DQw2 |
| (6D6+/CD8+:9%) | A11, B40, | :DR10, | DQw1 |

*Percentage of CD8+ T cells that express Vα12.1 by surface staining with mAb 6D6.
**Confirmed with molecular probe.

As shown in Table 2, no common class I was found to associate specifically with this group of patients. The majority (>90%) of both the Vα12.1-elevated and the Vα12.1-normal group of patients expressed HLA-DR1 and -DR4 alleles as expected for adult rheumatoid arthritis patients. Surprisingly, however, among the Vα12.1 elevated group of patients, the HLA-DQw2 allele was increased, as shown by the determination that 7 out of 8, or approximately 88% of the patients.

In general, the proportion of the DQW2 allele is approximately one in three (depending upon ethnic background) and likewise, about 30% of the Vα12.1 normal group of RA patients were DQw2-positive. The association of HLA-DQw2 occurrence in the Vα12.1-elevated individuals was highly significant (chi square=11.4 p<.001). The high frequency of HLA-DQw2 in the Vα12.1 elevated group of patients implicates this class II molecule in the RA disease process. The expanded CD8+ T cells may be class II (DQw2) -restricted, or alternatively, are possibly reactive to DQw2-derived peptides recognized in the context of class I MHC molecules.

Example 7

In this Example Vα12+CD8+ T cell clones were established and characterized. It was demonstrated that contacting peripherial blood mononuclear cells (PBMC) isolated from rheumatoic arthritis (RA) patients with a Vα12 specific mAB, 6D6, resulted in a rapid decrease in the number of Vα12+CD8+ T cells.

Vα12+CD8+ T cell clones were established that are representative of the clonally expanded population of T cells in vivo.

Peripheral blood mononuclear cells (PBMC) were isolated from rheumatoid arthritis (RA) patients with clonal and oligoclonal expansions of Vα12+CD8+ T cells. The expanded population of cells from one RA patient (ML) were purified by two color fluorescence activated cell sorting using monoclonal antibodies specific for the Vα12 and Vβ5.1 T cell receptor (TCR) variable regions, which were the Vα and Vβ chains used by the clonally expanded population of CD8+ T cells in this patient. These purified T cells were cloned by limiting dilution using allogeneic feeders, IL-2 and PHA. Five Vα12+CD8+ T cell clones were obtained. The junctional region sequences of the rearranged Vα and Vβ genes used by the T cell clones were identical to the sequence that had previously been determined for the clonally expanded population of circulating T cells from this patient.

The Vα12+CD8+ T cell clones are autoreactive

Figure 6:
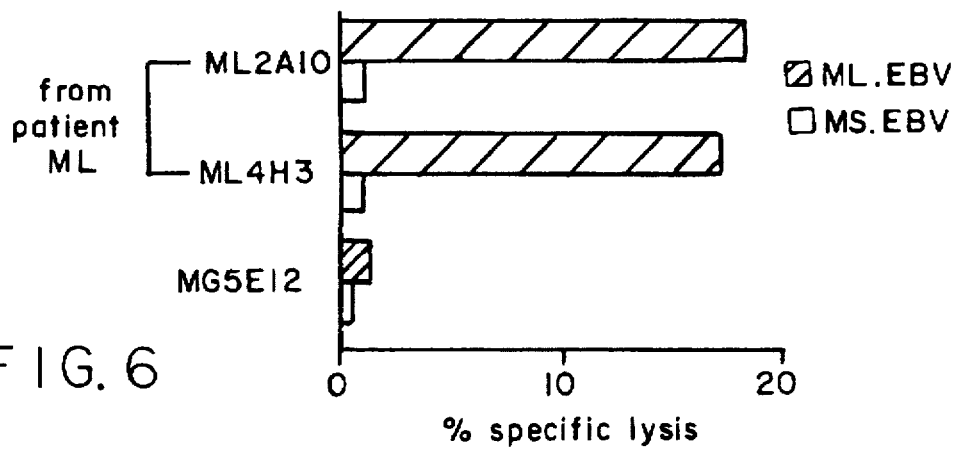
FIG. 6 illustrates $V\alpha 12^+CD8^+$ T cell clones derived from patient ML lyse autologous target cells. Autologous (ML.EBV) or allogeneic (MS.EBV) B lymphoblastoid cells were labeled with $Na51Cr$ and then used as target cells in a standard cytolytic assay. The $^{51}Cr$ labeled target cells were incubated with the T cell clones, and after four hours the amount of $Na^{51}Cr$ released into the supernatant was determined and the specific lysis calculated. The E:T ratio was 12.5:1.
Figure 7:
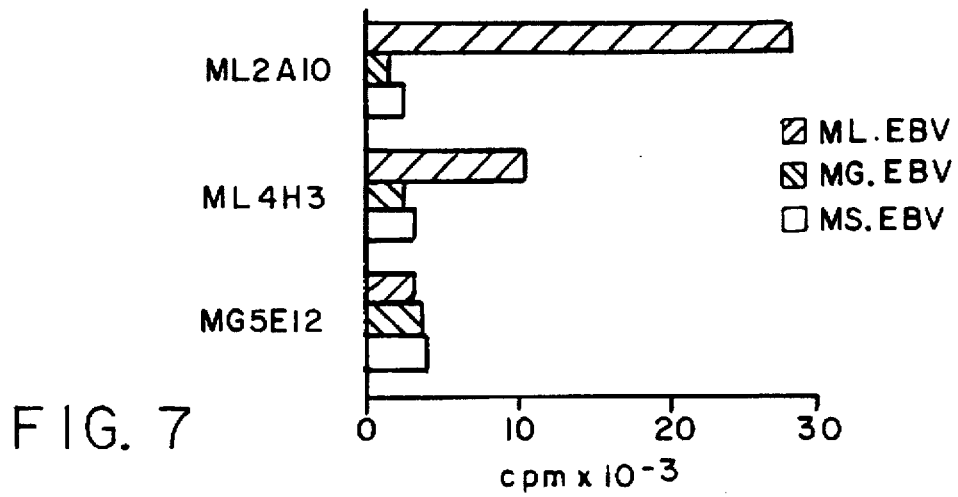
FIG. 7 illustrates that $V\alpha 12^+CD8^+$ T cell clones derived from patient ML proliferate when stimulated with autologous target cells. $5\times 10^4$ T cells and $5\times 10^4$ B-LCL were cultured together for 72 hours. $^3H$-thymidine incorporation during the last 6 hours of culture was determined and used as a measure of T cell proliferation.
Figure 8:
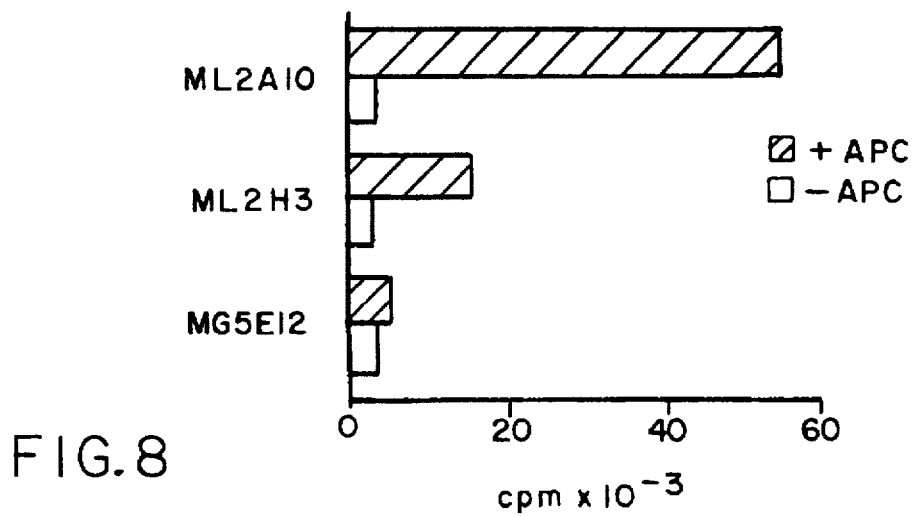
FIG. 8 illustrates that $V\alpha 12^+CD8^+$ T cell clones derived from patient ML secrete IL-2 when stimulated with autologous target cells. $5\times 10^4$ $V\alpha 12^+CD8^+$ T cells were cultured with $5\times 10^4$ autologous B-LCL (ML.EBV). After 24 hours, the amount of IL-2 produced by the T cells was assessed by determining whether the supernatants obtained from these cultures supported the proliferation of the IL-2 dependent CTLL-20 T cell line.

The Vα12+CD8+ T cell clones specifically recognized an autologous B lymphoblastoid cell line (B-LCL) that was derived by Epstein Barr virus infection of peripheral blood mononuclear cells from patient ML. The autoreactive nature of these T cells was based on three criteria: (1) lysis of an autologous cell line, but not a MHC-mismatched control cell line, in a cytolytic or "killing" assay (FIG. 6); (2) secretion of IL-2 (FIG. 8) and (3) proliferation when the T cell clones were stimulated with an autologous cell line (FIG. 7).

The T cell clones are restricted by class 1 MHC molecules

Figures 9, 10:
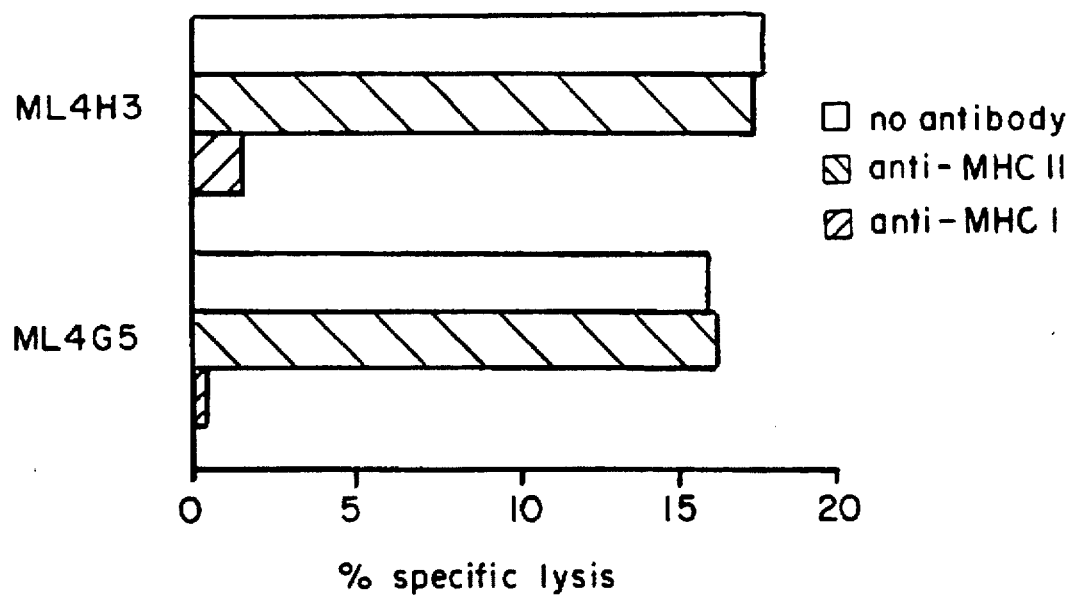
FIG. 9 illustrates that $V\alpha 12^+CD8^+$ T cell clones are restricted by class 1 MHC molecules. Antibodies to MHC class 1 molecules (W6/32) blocked the lysis of autologous target cells (ML.EBV) by the $V\alpha 12^+CD8^+$ T cell clones (ML4H3 and ML4G5). Antibodies to MHC class II molecules (L243, IVA12) did not block the lysis of the target cells.
FIG. 10 illustrates that the HLA-B60, -Cw3, -DQ2 extended haplotype is sufficient for recognition by the $V\alpha 12^+CD8^+$ T cell clones. A panel of B-LCL with diverse HLA types were used to stimulate the T cell clones MS2A10 and ML4H3. Three B lymphoblastoid cell lines were identified that were able to stimulate the proliferation of the two $V\alpha 12^+CD8^+$ T cell clones but not a random T cell clone. The three B-LCL share the HLA-B60, -Cw3, and -DQ2.

Antibody blocking experiments demonstrated that the Vα12+ CD8+ T cell clones were restricted by class 1 MHC molecules (FIG. 9). To further define the MHC restriction of these T cell clones, a panel of EBV transformed B lymphoblastoid cell lines (B-LCL) that shared one or more HLA alleles with the patient, were used as antigen presenting cells for the functional assays listed above. Using this approach, three HLA alleles were defined that are necessary for T cell recognition: HLA-B60, -Cw3, and -DQ2 (FIG. 10). The T cell clones will recognize other B-LCL that express this extended haplotype.

Figures 11A, 11B:
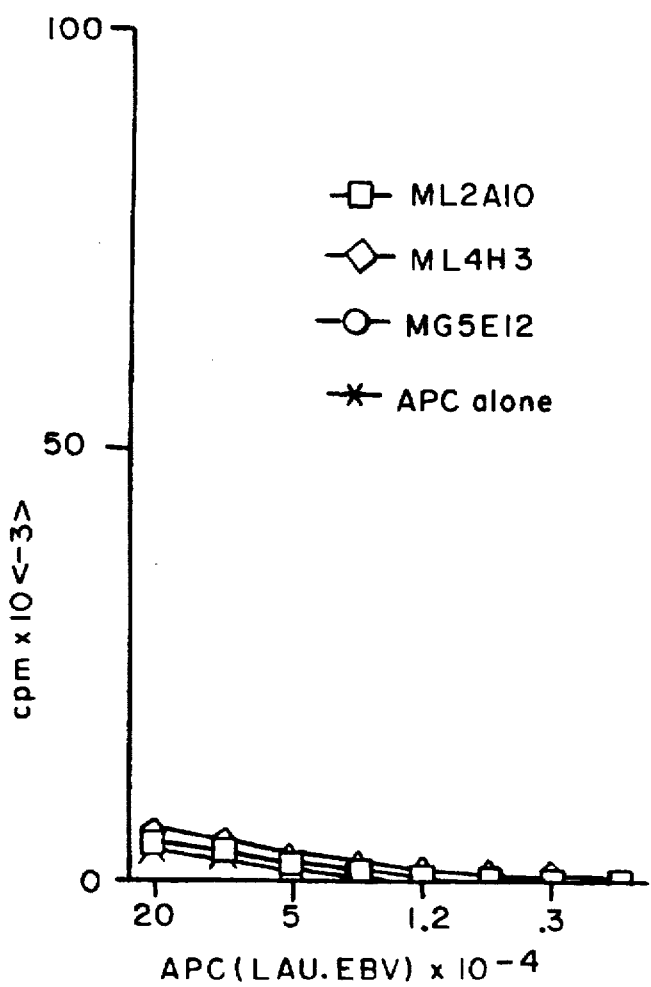
FIG. 11A and FIG. 11B illustrate that expression of HLA-DQ2 by the antigen presenting cell is necessary to stimulate the proliferation of the ML CD8+ $V\alpha 12+$ T cell clones. The B-LCL LAU.EBV is $HLA-B60^+Cw3^+$ but HLA-DQ2-. It did not stimulate the proliferation of the $V\alpha 12^+CD8^+$ T cell clones. This finding suggests that HLA-DQ2 is required for the activation of the $V\alpha 12^+CD8^+$ T cell clones.
Figure 12A:
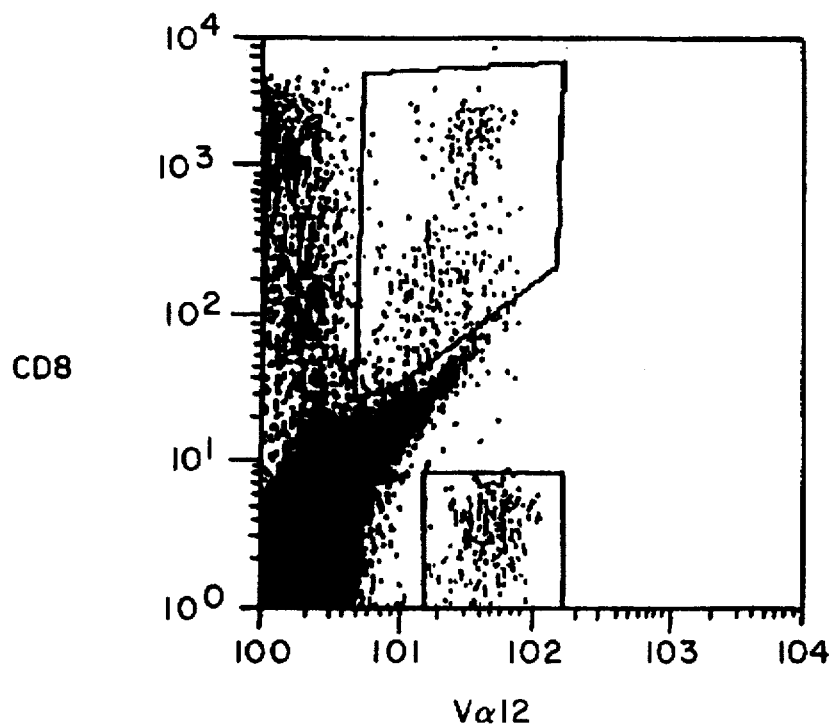
FIG. 12A and FIG. 12B illustrate that binding of the 6D6 monoclonal antibody to the $V\alpha 12^+CD8^+$ T cells ex vivo induces their apoptosis. Peripheral blood mononuclear cells were isolated from RA patients with expansions of $V\alpha 12^+$ $CD8^+$ T cells and cultured in 96 wellplates coated with the 6D6 monoclonal antibody. After 24–48 hours, the cells were recovered and stained with fluorescently labeled anti-$V\alpha 12$ and anti-CD8 antibodies. The percentage of $V\alpha 12^+T$ cells having undergone apoptosis was determined by counterstaining with 7-aminoactinomycin D.
Figure 12B:
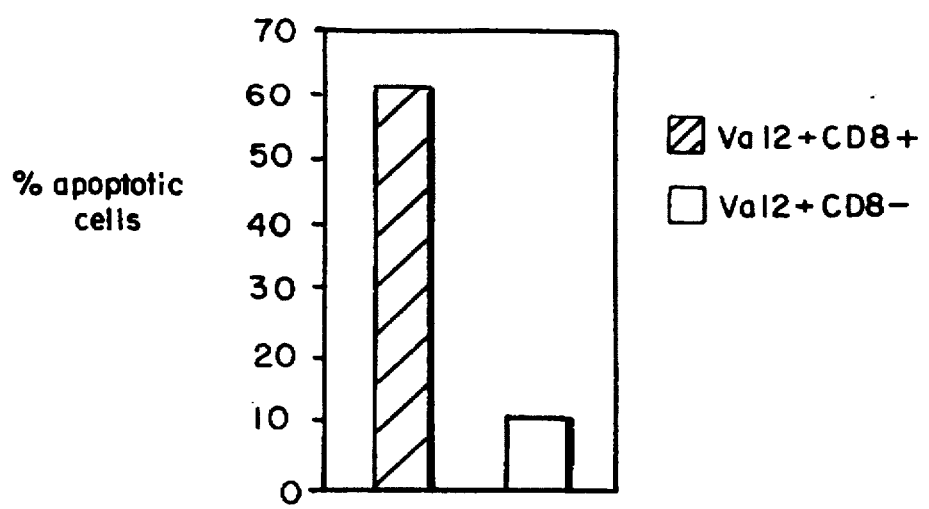

The presence of HLA-DQ2 was necessary for T cell recognition (FIG. 11A and 11B)

B lymphoblastoid cell lines that expressed HLA-B60, -Cw3 and -DQ2 were recognized by the T cell clones. In contrast, B-LCL that expressed HLA-B60 and HLA-Cw3 but lacked HLA-DQ2 (i.e., B60+ Cw3+ DQ2−) failed to stimulate T cell proliferation. As these T cells were restricted by class 1 MHC molecules (i.e., HLA-B60 or HLA-Cw3), the requirement for the presence of HLA-DQ2 suggests that the autoreactive T cells are recognizing a peptide derived from the alpha or beta chain of the HLA-DQ2 protein which is presented by HLA-B60 or -Cw3.

The 6D6 mAb induced apoptosis of the T cells in vitro

Vα12+ T cells account for only a few percent CD8+ T cells in normal individuals; however, when PBMC from normal individuals are treated with the Vα12 specific mAb 6D6 in vitro, Vα12+ T cells expand to account for up to 60% of the CD8+ T cells (FIG. 12A). No change in the percentage of Vα12/CD8+ T cells occurs after stimulation with either anti-CD3 or a control immunoglobulin. In contrast, Vα12+ T cells account for up to 65% of the CD8+ T cells in vivo. When PBMC from such RA patients are stimulated with the 6D6 mAb or an anti-CD3 mAb, the starting population of Vα12+ CD8+ T cells rapidly falls off to 20% by day four (FIG. 12B). This suggests that the starting population of Vα12+ T cells is either dying or failing to proliferate when stimulated with anti-CD3 or anti-Vα12+ T cells emerges, proliferates, and expands. This now appears to be secondary to the ability of the 6D6 mAb to induce apoptosis of the Vα12+ T cells in vitro. The expanded population of Vα12+ CD8+ T cells may be more susceptible to apoptosis than other circulating T cells, and that this property may be a reflection of the activation state of the T cells.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 72 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
( A ) ORGANISM: Homo sapien
( D ) DEVELOPMENTAL STAGE: adult
( G ) CELL TYPE: peripheral blood CD8+T lymphocytes ( v i i ) IMMEDIATE SOURCE:
( A ) LIBRARY: cDNA
( B ) CLONE: clone #'s MLα 1.01 to Mlα 1.15.

( v i i ) POSITION IN GENOME:
( A ) CHROMOSOME/SEGMENT: 14q ( v i i i ) FEATURE:
( A ) NAME/KEY: T cell receptor alpha gene - JαAF211
( B ) LOCATION: 17 - 72
( C ) IDENTIFICATION METHOD: similarity with known sequence
( D ) OTHER INFORMATION: Nucleotides 1-12 comprise the 3' nucleotides of the rearranged T cell receptor V region Vα12.1. Nucleotides 13-16 are contributed by template independent insertions.

( x ) PUBLICATION INFORMATION:
( A ) AUTHORS: KLEIN et al.
( B ) TITLE: Diversity and structure of human T-cell receptor alpha chains.
( C ) JOURNAL: Proc. Natl. Acad. Sci.
( D ) VOLUME: 84
( F ) PAGES: 6884
( G ) DATE: 1987
( K ) RELEVANT RESIDUES IN SEQ ID NO:1: FROM 17 TO 72

( x i ) SEQUENCE DESCRIPTION: SEQ ID NO:1:
```
TGT GCT CTG AGT GAT GGC TAT GGT CAG AAT TTT      33
CYS ALA LEU SER ASP GLY TYR GLY GLN ASN PHE
1               5                   10
GTC TTT GGT CCC GGA ACC AGA TTG TCC GTG CTG      66
VAL PHE GLY PRO GLY THR ARG LEU SER VAL LEU
15                      20
CCC TAT                                          72
PRO TYR
```

( 2 ) INFORMATION FOR SEQ ID NO:2:

( i ) SEQUENCE CHARACTERISTICS:
( A ) LENGTH: 78 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:

(A) ORGANISM: Homo sapien
(D) DEVELOPMENTAL STAGE: adult
(E) HAPLOTYPE:
(G) CELL TYPE: peripheral blood CD8+T lymphocytes (vii) IMMEDIATE SOURCE:
(A) LIBRARY: cDNA
(B) CLONE: clone #'s EBα 6.01, 6.02, 6.04,
6.06, 6.07, 6.10, 6.11, 6.12, and 6.13.

(vii) POSITION IN GENOME:
(A) CHROMOSOME/SEGMENT: 14q (viii) FEATURE:
(A) NAME/KEY: T cell receptor alpha gene JαA12
(B) LOCATION: 17 to 78
(C) IDENTIFICATION METHOD: similarity with known
sequence
(D) OTHER INFORMATION: Nucleotides 1- 12 comprise
the 3' nucleotides of the rearranged T cell receptor V re
Vα12.1. Nucleotides 13-16 are contributed by template ind
insertions.

(x) PUBLICATION INFORMATION:
(A) AUTHORS: Koop et al.
(B) TITLE: Nucleotide Sequence of the 3' Terminal
End of the TCR α/k locus.
(C) JOURNAL: Unpublished
(D) VOLUME:
(F) PAGES:
(G) DATE: 1992
(K) RELEVANT RESIDUES IN SEQ ID NO:2:
FROM 17 TO 78

(xi) SEQUENCE DESCRIPTION: SEQ ID NO:2:
```
TGT GCT CTG AGT GAT TAT CAG GGC GGA TCT GAA         33
CYS ALA LEU SER ASP TYR GLN GLY GLY SER GLU
1                 5                   10
AAG CTG GCT TTT GGA AAG GGA ATG AAA CTG ACA         66
LYS LEU VAL PHE GLY LYS GLY MET LYS LEU THR
15                      20
GTA AAC CCA TAT                                      78
VAL ASN PRO TYR
25
```

(2) INFORMATION FOR SEQ ID NO:3:

(i) SEQUENCE CHARACTERISTICS:
(A) LENGTH: 72 base pairs
(B) TYPE: nucleic acid
(C) STRANDEDNESS: double
(D) TOPOLOGY: linear (ii) MOLECULE TYPE: cDNA to mRNA (iii) HYPOTHETICAL: no (iv) ANTI-SENSE: no (vi) ORIGINAL SOURCE:
(A) ORGANISM: Homo sapien
(D) DEVELOPMENTAL STAGE: adult
(G) CELL TYPE: peripheral blood CD8+T lymphocytes (vii) IMMEDIATE SOURCE:
(A) LIBRARY: cDNA
(B) CLONE: clone #'s MGα 1.01, 1.02, 1.04, 1.08,
1.09, 1.14, 1.15, 1.16, 1.17, 1.19, 1.25,
1.27, 1.28, 1.31, 1.34, 1.37.

(vii) POSITION IN GENOME:
(A) CHROMOSOME/SEGMENT: 14q (viii) FEATURE:
(A) NAME/KEY: T cell receptor alpha gene JαA6
(B) LOCATION: 13 - 72
(C) IDENTIFICATION METHOD: similarity with known
sequence
(D) OTHER INFORMATION: Nucleotides 1-11 comprise
the 3' nucleotides of the rearranged T cell receptor V re Vα12.1. Nucleotide 12 is
a template independent nucleotide insertion.

( x ) PUBLICATION INFORMATION:
    ( A ) AUTHORS: TOYONAGO et al.
    ( B ) TITLE: Genes of the T-cell antigen receptors
        in normal and malignant T cells.
    ( C ) JOURNAL: Ann. Rev. Immunol.
    ( D ) VOLUME: 5
    ( F ) PAGES: 585-620
    ( G ) DATE: 1987
    ( K ) RELEVANT RESIDUES IN SEQ ID NO:3:
        FROM 13 TO 72

( x i ) SEQUENCE DESCRIPTION: SEQ ID NO:3:

```
TGT  GCT  CTG  AGA  GGG  GGA  GGT  GCT  GAC  GGA  CTC      33
CYS  ALA  LEU  ARG  GLY  GLY  GLY  ALA  ASP  GLY  LEU
 1              5                        10

ACC  TTT  GGC  AAA  GGG  ACT  CAT  CTA  ATC  ATC  CAG      66
THR  PHE  GLY  LYS  GLY  THR  HIS  LEU  ILE  ILE  GLN
               15                        20

CCC  TAT                                                   72
PRO  TYR
```

( 2 ) INFORMATION FOR SEQ ID NO:4:

( i ) SEQUENCE CHARACTERISTICS:
        ( A ) LENGTH: 84 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: Homo sapien
        ( D ) DEVELOPMENTAL STAGE: adult
        ( G ) CELL TYPE: peripheral blood CD8+T lymphocytes ( v i i ) IMMEDIATE SOURCE:
        ( A ) LIBRARY: cDNA
        ( B ) CLONE: clone #'s MGα 1.07, 1.21, 1.23

( v i i ) POSITION IN GENOME:
        ( A ) CHROMOSOME/SEGMENT: 14q ( v i i i ) FEATURE:
        ( A ) NAME/KEY: T cell receptor alpha gene JαA6
        ( B ) LOCATION: 19 - 84
        ( C ) IDENTIFICATION METHOD: similarity with known
            sequence
        ( D ) OTHER INFORMATION: Nucleotides 1- 14 comprise
            the 3' nucleotides of the rearranged T cell receptor V re
            Vα12.1. Nucleotides 15-18
            are template independent insertions.

( x ) PUBLICATION INFORMATION:
    ( A ) AUTHORS: TOYONAGO et al.
    ( B ) TITLE: Genes of the T-cell antigen receptors in
        normal and malignant T cells.
    ( C ) JOURNAL: Ann. Rev. Immunol.
    ( D ) VOLUME: 5
    ( F ) PAGES: 585-620
    ( G ) DATE: 1987
    ( K ) RELEVANT RESIDUES IN SEQ ID NO:3:
        FROM 19 TO 84

( x i ) SEQUENCE DESCRIPTION: SEQ ID NO:4:

```
TGT  GCT  CTG  AGT  GAG  CCT  TAT  TCA  GGA  GGA  GGT      33
CYS  ALA  LEU  SER  GLU  PRO  TYR  SER  GLY  GLY  GLY
 1              5                        10

GCT  GAC  GGA  CTC  ACC  TTT  GGC  AAA  GGG  ACT  CAT      66
```

|     |     |     |     |     |     |     |     |     |     |     |     |
|-----|-----|-----|-----|-----|-----|-----|-----|-----|-----|-----|-----|
| ALA | ASP | GLY | LEU | THR | PHE | GLY | LYS | GLY | THR | HIS |     |
| 15  |     |     |     |     | 20  |     |     |     |     |     |     |
| CTA | ATC | ATC | CAG | CCC | TAT |     |     |     |     |     | 84  |
| LEU | ILE | ILE | GLN | PRO | TYR |     |     |     |     |     |     |
| 25  |     |     |     |     |     |     |     |     |     |     |     |

( 2 ) INFORMATION FOR SEQ ID NO:5:

( i ) SEQUENCE CHARACTERISTICS:
        ( A ) LENGTH: 72 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: Homo sapien
        ( D ) DEVELOPMENTAL STAGE: adult
        ( G ) CELL TYPE: peripheral blood CD8+T lymphocytes ( v i i ) IMMEDIATE SOURCE:
        ( A ) LIBRARY: cDNA
        ( B ) CLONE: clone #'s MLα 1- 9

( v i i ) POSITION IN GENOME:
        ( A ) CHROMOSOME/SEGMENT: 14q ( v i i i ) FEATURE:
        ( A ) NAME/KEY: T cell receptor alpha gene JαA1
        ( B ) LOCATION: 17 - 72
        ( C ) IDENTIFICATION METHOD: similarity with known
            sequence
        ( D ) OTHER INFORMATION: Nucleotides 1- 12 comprise
            the 3' nucleotides of the rearranged T cell
            receptor V region Vα12.1. Nucleotides 13-16
            are template independent insertions.

( x ) PUBLICATION INFORMATION:
        ( A ) AUTHORS: KLEIN et al.
        ( B ) TITLE: Diversity and structure of human T-cell
            receptor alpha chains.
        ( C ) JOURNAL: Proc. Natl. Acad. Sci.
        ( D ) VOLUME: 84
        ( F ) PAGES: 6884
        ( G ) DATE: 1987
        ( K ) RELEVANT RESIDUES IN SEQ ID NO:1:
            FROM 17 TO 72

( x i ) SEQUENCE DESCRIPTION: SEQ ID NO:5:

|     |     |     |     |     |     |     |     |     |     |     |     |
|-----|-----|-----|-----|-----|-----|-----|-----|-----|-----|-----|-----|
| TGT | GCT | CTG | AGT | GAC | GGC | TAT | GGT | CAG | AAT | TTT | 33  |
| CYS | ALA | LEU | SER | ASP | GLY | TYR | GLY | GLN | ASN | PHE |     |
| 1   |     |     |     | 5   |     |     |     |     | 10  |     |     |
| GTC | TTT | GGT | CCC | GGA | ACC | AGA | TTG | TCC | GTG | CTG | 66  |
| VAL | PHE | GLY | PRO | GLY | THR | ARG | LEU | SER | VAL | LEU |     |
| 15  |     |     |     |     | 20  |     |     |     |     |     |     |
| CCC | TAT |     |     |     |     |     |     |     |     |     | 72  |
| PRO | TYR |     |     |     |     |     |     |     |     |     |     |

( 2 ) INFORMATION FOR SEQ ID NO:6:

( i ) SEQUENCE CHARACTERISTICS:
        ( A ) LENGTH: 72 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:

(A) ORGANISM: Homo sapien
(D) DEVELOPMENTAL STAGE: adult
(G) CELL TYPE: peripheral blood CD8+T lymphocytes (vii) IMMEDIATE SOURCE:
    (A) LIBRARY: cDNA
    (B) CLONE: clone #'s MGα 3, 5, 6, 10, 15, 16,
        17, 20, 21- 29, 31, 32, 34

(vii) POSITION IN GENOME:
    (A) CHROMOSOME/SEGMENT: 14a (viii) FEATURE:
    (A) NAME/KEY: T cell receptor alpha gene JαA6
    (B) LOCATION: 10-70
    (C) IDENTIFICATION METHOD: similarity with
        known sequence
    (D) OTHER INFORMATION: Nucleotides 1-11 comprise
        the 3' nucleotides of the rearranged T cell receptor V re
        Vα12.1. Nucleotide 12 is a
        template independent insertion.

(x) PUBLICATION INFORMATION:
    (A) AUTHORS: TOYONAGO et al.
    (B) TITLE: Genes of the T-cell antigen receptors
        in normal and malignant T cells.
    (C) JOURNAL: Ann. Rev. Immunol.
    (D) VOLUME: 5
    (F) PAGES: 585-620
    (G) DATE: 1987
    (K) RELEVANT RESIDUES IN SEQ ID NO:3:
        FROM 13 TO 72

(xi) SEQUENCE DESCRIPTION: SEQ ID NO:6:

```
TGT GCT CTG AGA GGG GGA GGT GCT GAC GGA CTC      33
CYS ALA LEU ARG GLY GLY GLY ALA ASP GLY LEU
1            5                       10
ACC TTT GGC AAA GGG ACT CAT CTA ATC ATC CAG      66
THR PHE GLY LYS GLY THR HIS LEU ILE ILE GLN
15                  20
CCC TAT                                          72
PRO TYR
```

(2) INFORMATION FOR SEQ ID NO:7:

(i) SEQUENCE CHARACTERISTICS:
    (A) LENGTH: 84 base pairs
    (B) TYPE: nucleic acid
    (C) STRANDEDNESS: double
    (D) TOPOLOGY: linear (ii) MOLECULE TYPE: cDNA to mRNA (iii) HYPOTHETICAL: no (iv) ANTI-SENSE: no (vi) ORIGINAL SOURCE:
    (A) ORGANISM: Homo sapien
    (D) DEVELOPMENTAL STAGE: adult
    (G) CELL TYPE: peripheral blood CD8+T lymphocytes (vii) IMMEDIATE SOURCE:
    (A) LIBRARY: cDNA
    (B) CLONE: clone #'s MGα 1, 9, 13, 18, 30

(vii) POSITION IN GENOME:
    (A) CHROMOSOME/SEGMENT: 14q (viii) FEATURE:
    (A) NAME/KEY: T cell receptor alpha gene JαA6
    (B) LOCATION: 19-84
    (C) IDENTIFICATION METHOD: similarity with
        known sequence
    (D) OTHER INFORMATION: Nucleotides 1- 14 comprise
        the 3' nucleotides of the rearranged T cell receptor V re
        Vα12.1. Nucleotides 15-
        18 are template independent insertions.

(x) PUBLICATION INFORMATION:
  (A) AUTHORS: TOYONAGO et al.
  (B) TITLE: Genes of the T-cell antigen receptors in normal and malignant T cells.
  (C) JOURNAL: Ann. Rev. Immunol.
  (D) VOLUME: 5
  (F) PAGES: 585-620
  (G) DATE: 1987
  (K) RELEVANT RESIDUES IN SEQ ID NO:3:
      FROM 19 TO 84

(xi) SEQUENCE DESCRIPTION: SEQ ID NO:7:

```
TGT GCT CTG AGT GAG CCT TAT TCA GGA GGA GGT      33
CYS ALA LEU SER GLU PRO TYR SER GLY GLY GLY
1               5                   10
GCT GAC GGA CTC ACC TTT GGC AAA GGG ACT CAT      66
ALA ASP GLY LEU THR PHE GLY LYS GLY THR HIS
15                      20
CTA ATC ATC CAG CCC TAT                          84
LEU ILE ILE GLN PRO TYR
25
```

We claim:

1. A method of treating rheumatoid arthritis in a host showing an elevated level of Vα12.1 on T-cells as compared to a baseline of normal hosts comprising administering a therapeutically effective amount of a Vα12.1 specific antibody to said host.

2. A method according to claim 1 wherein the antibody is a monoclonal antibody, fragment, or derivative thereof reactive with an epitope of the Vα12.1 gene product.

3. A method according to claim 2, wherein the antibody is 6D6.

4. A method according to claim 1, wherein the antibody is conjugated to a substance selected from the group consisting of radionucleotides, toxins and cytotoxic drugs.

5. The method of claim 1 wherein the host is a human.

6. A method for treating an individual afflicted with an autoimmune disease showing an elevation of Vα12.1 on T-cells which comprises administering a therapeutically effective amount of a Vα12.1 specific antibody to said host.

7. A method according to claim 6, wherein the antibody is 6D6.

* * * * *